United States Patent
Scheller et al.

(10) Patent No.: US 9,763,830 B2
(45) Date of Patent: *Sep. 19, 2017

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 438 days.

This patent is subject to a terminal disclaimer.

(21) Appl. No.: 14/026,051

(22) Filed: Sep. 13, 2013

(65) Prior Publication Data

US 2014/0107628 A1   Apr. 17, 2014

Related U.S. Application Data

(60) Provisional application No. 61/713,519, filed on Oct. 13, 2012.

(51) Int. Cl.
  *A61F 9/008* (2006.01)

(52) U.S. Cl.
  CPC .......... *A61F 9/008* (2013.01); *A61F 9/00821* (2013.01); *A61F 2009/00863* (2013.01)

(58) Field of Classification Search
  CPC .................. A61F 9/008; A61F 9/00821; A61F 2009/00863; A61B 18/18

(Continued)

(56) References Cited

U.S. PATENT DOCUMENTS 4,147,443 A * 4/1979 Skobel ............... A61B 17/2841
                                                          30/343
5,190,050 A   3/1993 Nitzsche
(Continued)

FOREIGN PATENT DOCUMENTS

EP    EP 0900547 B1    3/1999
WO    WO 2006/091597 A1    8/2006

OTHER PUBLICATIONS

Melchels et al. A review on stereolithography and its applications in biomedical engineering, May 15, 2010, Biomaterials 31 (2010) 6121-6130, DOI: 10.1016/j.biomaterials.2010.04.050.*

(Continued)

*Primary Examiner* — Christopher A Flory
*Assistant Examiner* — Jonathan Kuo
(74) *Attorney, Agent, or Firm* — Kevin P. Rollins

(57) ABSTRACT

A steerable laser probe may include a handle, an actuation structure having an actuation structure distal end and an actuation structure proximal end, a housing tube, a first housing tube portion of the housing tube having a first stiffness, a second housing tube portion of the housing tube having a second stiffness, and an optic fiber disposed within an inner bore of the handle and the housing tube. An extension of the actuation structure distal end relative to the actuation structure proximal end may be configured to gradually curve the housing tube and the optic fiber. A retraction of the actuation structure distal end relative to the actuation structure proximal end may be configured to gradually straighten the housing tube and the optic fiber.

20 Claims, 27 Drawing Sheets

(58) Field of Classification Search
USPC .................................................. 606/4, 13–16
See application file for complete search history.

(56) References Cited

U.S. PATENT DOCUMENTS

| | | | |
|---|---|---|---|
| 5,355,871 A | 10/1994 | Hurley et al. | |
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 6,123,699 A | 9/2000 | Webster, Jr. | |
| 6,126,654 A | 10/2000 | Giba et al. | |
| 6,198,974 B1 | 3/2001 | Webster, Jr. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,551,302 B1 | 4/2003 | Rosinko et al. | |
| 6,572,608 B1 | 6/2003 | Lee et al. | |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,984,230 B2 | 1/2006 | Scheller et al. | |
| 7,004,957 B1 | 2/2006 | Dampney et al. | |
| 7,303,533 B2 | 12/2007 | Johansen et al. | |
| 7,402,158 B2 | 7/2008 | Scheller et al. | |
| 7,555,327 B2 * | 6/2009 | Matlock | A61B 5/14552 600/344 |
| 7,632,242 B2 | 12/2009 | Griffin et al. | |
| 7,766,904 B2 | 8/2010 | Mc Gowan, Sr. et al. | |
| 7,935,108 B2 * | 5/2011 | Baxter | A61B 18/1492 606/15 |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 9,138,350 B2 * | 9/2015 | Scheller | A61F 9/00821 |
| 9,149,389 B2 * | 10/2015 | Scheller | A61B 17/30 |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0157985 A1 | 7/2005 | McGowan, Sr. et al. | |
| 2005/0272975 A1 | 12/2005 | McWeeney et al. | |
| 2007/0185514 A1 * | 8/2007 | Kirchhevel | A61F 9/00763 606/171 |
| 2009/0018393 A1 | 1/2009 | Dick et al. | |
| 2009/0187170 A1 | 7/2009 | Auld et al. | |
| 2009/0312750 A1 | 12/2009 | Spaide | |
| 2010/0004642 A1 | 1/2010 | Lumpkin | |
| 2010/0268234 A1 | 10/2010 | Aho et al. | |
| 2010/0331883 A1 * | 12/2010 | Schmitz | A61B 10/0275 606/249 |
| 2011/0028947 A1 | 2/2011 | Scheller et al. | |
| 2012/0116361 A1 * | 5/2012 | Hanlon | A61B 17/3205 606/1 |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0096541 A1 | 4/2013 | Scheller et al. | |
| 2013/0116671 A1 | 5/2013 | Scheller et al. | |
| 2013/0150838 A1 | 6/2013 | Scheller et al. | |
| 2013/0165910 A1 | 6/2013 | Scheller et al. | |
| 2014/0107629 A1 * | 4/2014 | Scheller | A61F 9/00821 606/4 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

* cited by examiner

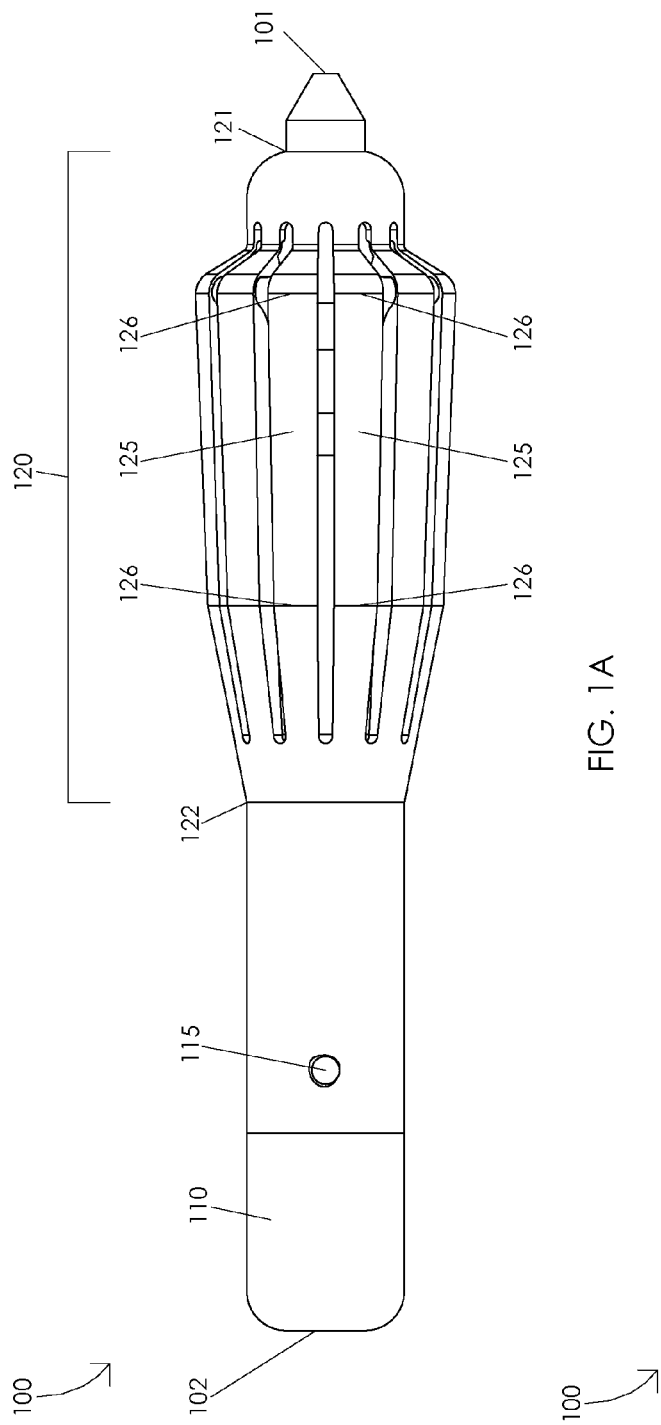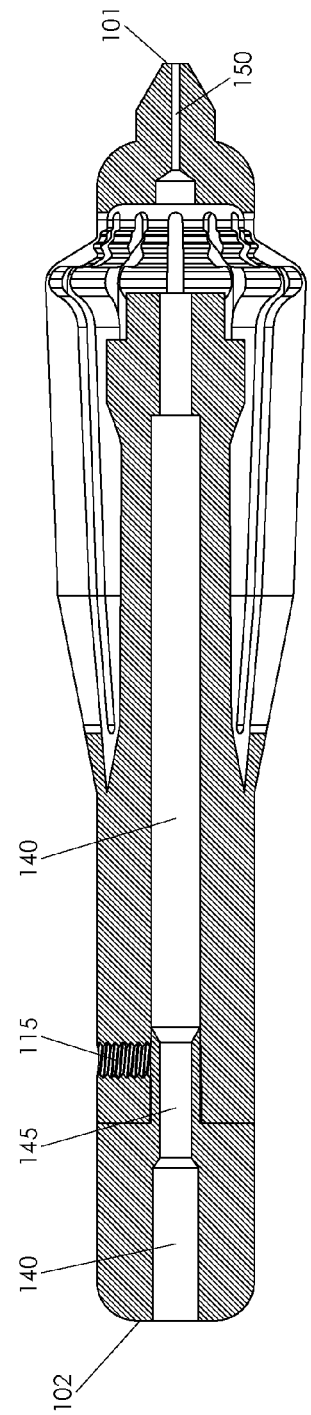
FIG. 1A
FIG. 1B

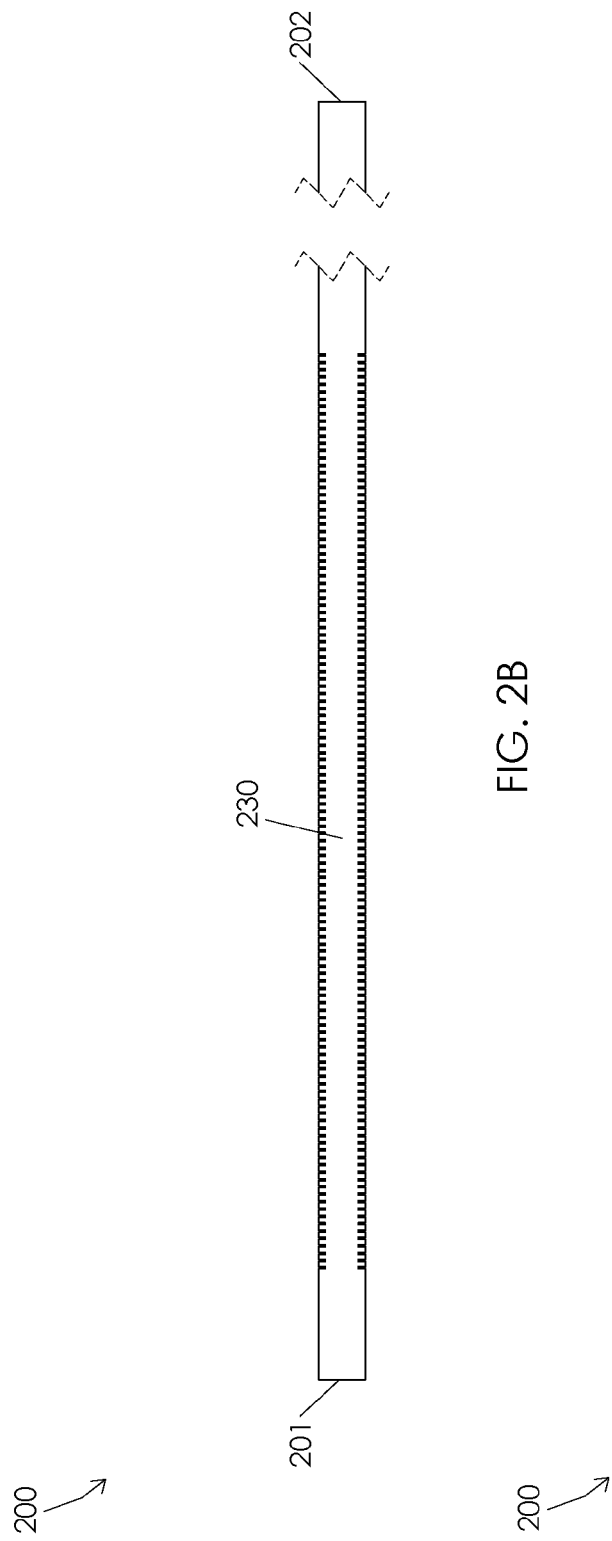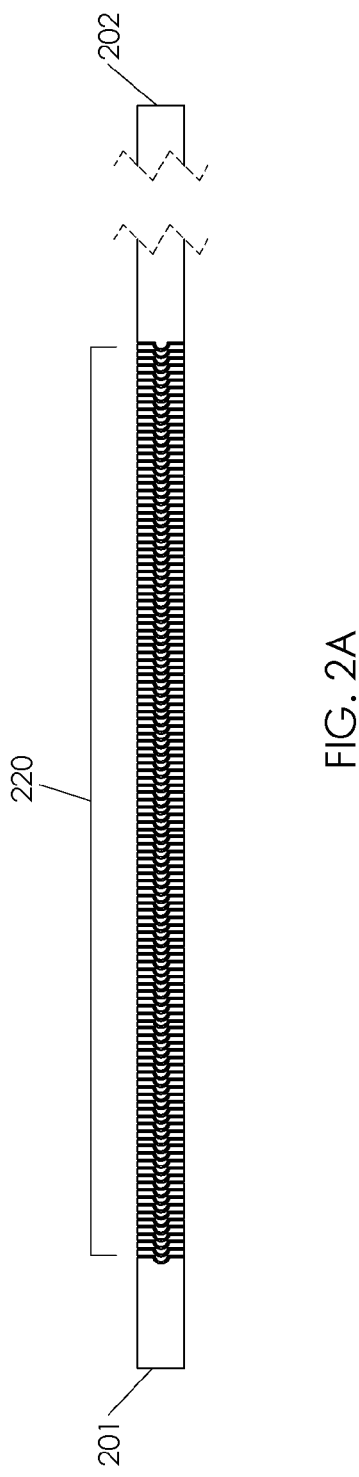

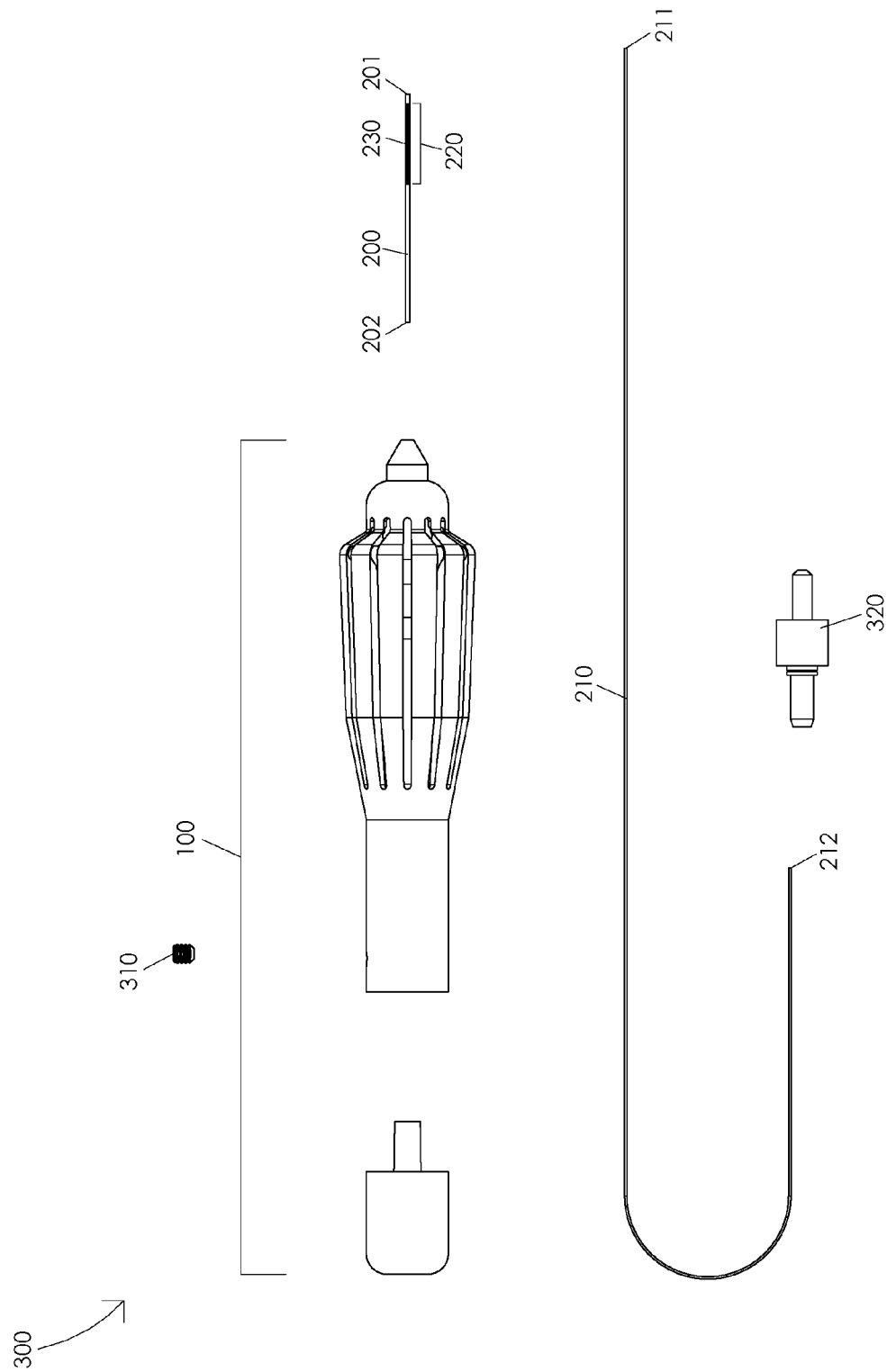

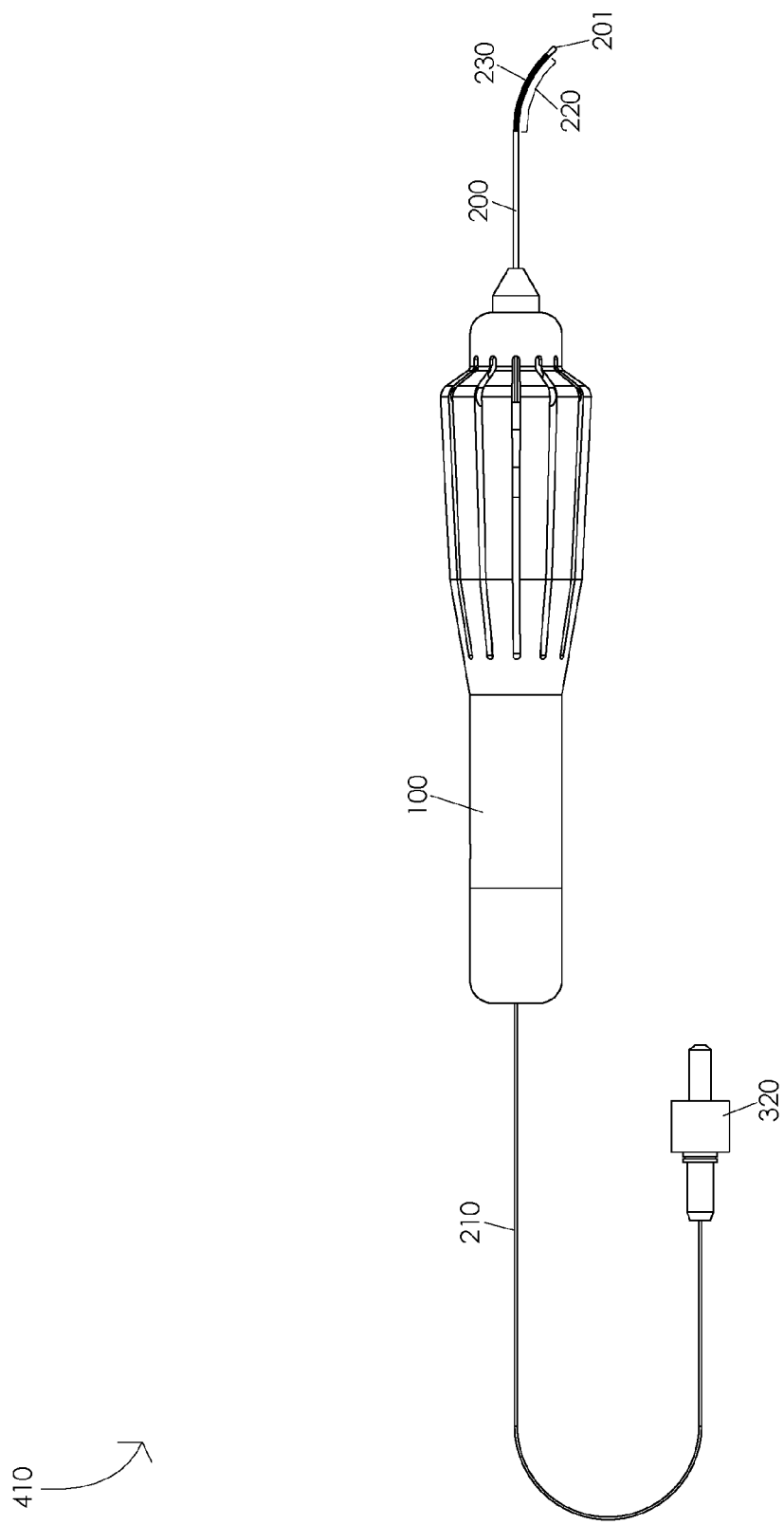

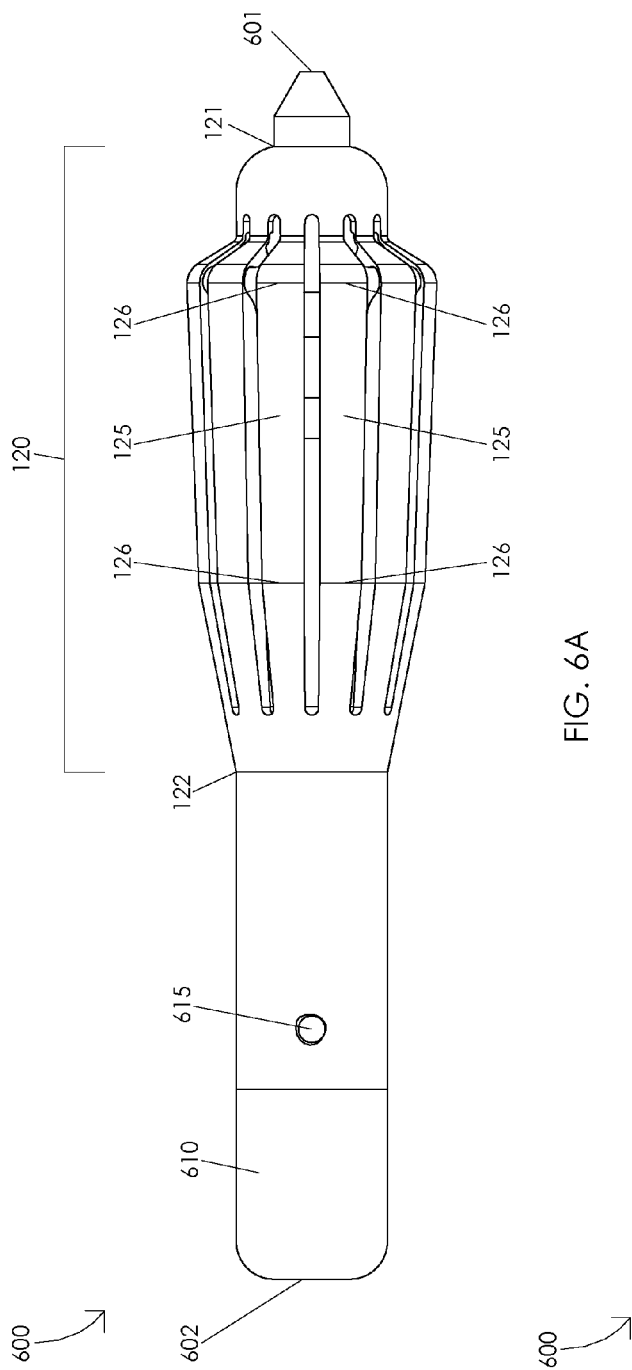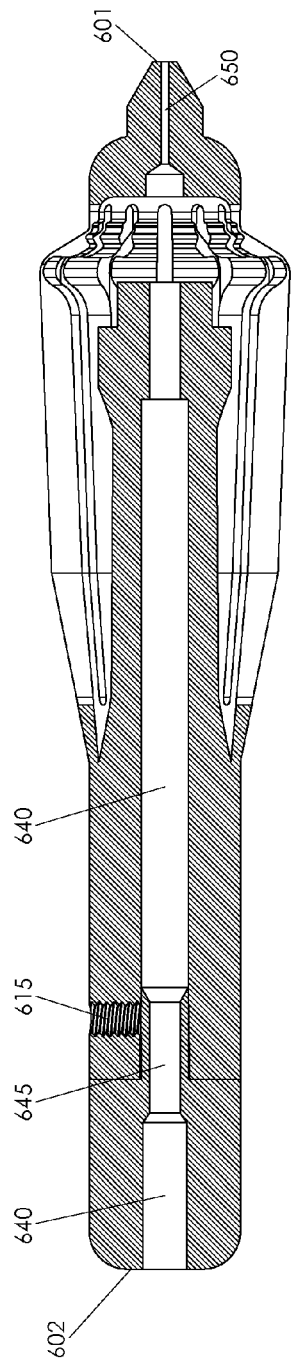
FIG. 6A
FIG. 6B

STEERABLE LASER PROBE

CROSS-REFERENCE TO RELATED APPLICATIONS

This Application claims the benefit of U.S. Provisional Application No. 61/713,519, filed Oct. 13, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle, an actuation structure having an actuation structure distal end and an actuation structure proximal end, a housing tube, a first housing tube portion of the housing tube having a first stiffness, a second housing tube portion of the housing tube having a second stiffness, and an optic fiber disposed within an inner bore of the handle and the housing tube. Illustratively, a compression of the actuation structure may be configured to extend the actuation structure distal end relative to the actuation structure proximal end. In one or more embodiments, an extension of the actuation structure distal end relative to the actuation structure proximal end may be configured to gradually curve the housing tube and the optic fiber. Illustratively, a decompression of the actuation structure may be configured to retract the actuation structure distal end relative to the actuation structure proximal end. In one or more embodiments, a refraction of the actuation structure distal end relative to the actuation structure proximal end may be configured to gradually straighten the housing tube and the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 2A, 2B, and 2C are schematic diagrams illustrating a housing tube;

FIG. 3 is a schematic diagram illustrating an exploded view of a steerable laser probe assembly;

FIGS. 4A, 4B, 4C, 4D, and 4E are schematic diagrams illustrating a gradual curving of an optic fiber;

FIGS. 6A and 6B are schematic diagrams illustrating a handle;

DETAILED DESCRIPTION OF AN ILLUSTRATIVE EMBODIMENT

Figure 2C:
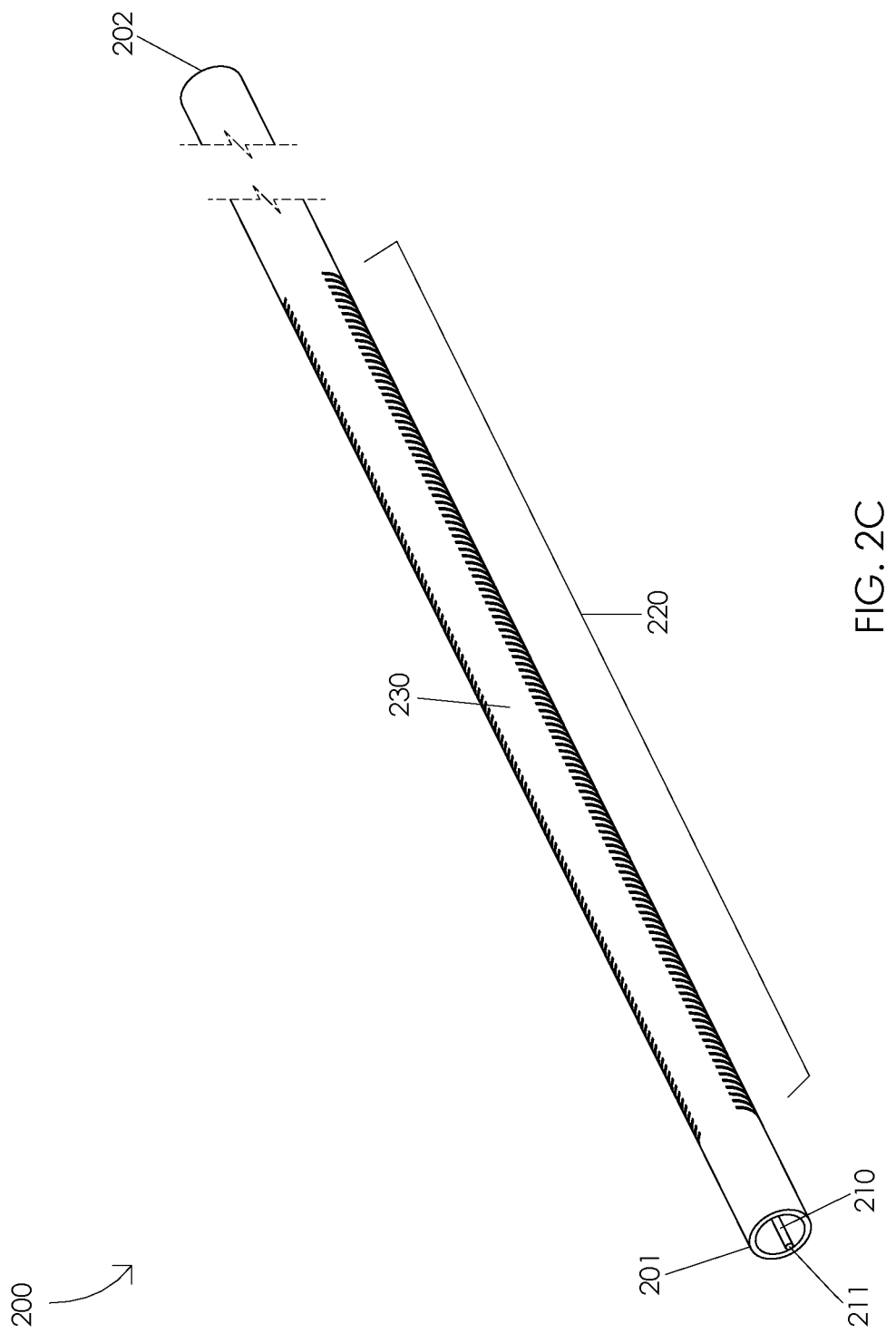

FIGS. 1A and 1B are schematic diagrams illustrating a handle 100. FIG. 1A illustrates a top view of a handle 100. Illustratively, handle 100 may comprise a handle distal end 101, a handle proximal end 102, a handle end plug 110, a fixation mechanism housing 115, and an actuation structure 120 having an actuation structure distal end 121 and an actuation structure proximal end 122. In one or more embodiments, actuation structure 120 may comprise a plurality of actuation arms 125. Illustratively, each actuation arm 125 of a plurality of actuation arms 125 may comprise one or more extension joints 126. In one or more embodiments, an application of a force to actuation structure 120 may be configured to compress actuation structure 120. For example, a surgeon may compress actuation structure 120 by applying a force to a portion of actuation structure 120. Illustratively, an application of a force to a portion of an actuation arm 125 of a plurality of actuation arms 125 may be configured to compress actuation structure 120. For example, a surgeon may compress actuation structure 120 by applying a force to a portion of an actuation arm 125 of a plurality of actuation arms 125.

In one or more embodiments, actuation structure 120 may be compressed by an application of one or more forces at one or more locations around an outer perimeter of actuation structure 120. Illustratively, the one or more locations may comprise any of a plurality of locations around the outer perimeter of actuation structure 120. For example, a surgeon may compress actuation structure 120 by squeezing actuation structure 120. Illustratively, the surgeon may compress actuation structure 120 by squeezing actuation structure 120 at any particular location of a plurality of locations around an outer perimeter of actuation structure 120. For example, a surgeon may rotate handle 100 and compress actuation structure 120 in any rotational orientation of a plurality of rotational oris entations of handle 100.

In one or more embodiments, a compression of actuation structure 120 may be configured to increase a distance between actuation structure distal end 121 and actuation structure proximal end 122. Illustratively, a compression of actuation structure 120 may be configured to extend actuation structure distal end 121 relative to actuation structure proximal end 122. In one or more embodiments, an application of a force having a magnitude in a range of 0.6 to 1.6 pounds to a portion of actuation structure 120 may be configured to compress actuation structure 120, e.g., an application of a force having a magnitude of 1.1 pounds to a portion of actuation structure 120 may be configured to compress actuation structure 120. Illustratively, an application of a force having a magnitude less than 0.6 pounds or greater than 1.6 pounds to a portion of actuation structure 120 may be configured to compress actuation structure 120. In one or more embodiments, a compression of actuation structure 120 may be configured to extend actuation structure distal end 121 in a range of 0.02 to 0.06 inches relative to actuation structure proximal end 122. Illustratively, a compression of actuation structure 120 may be configured to extend actuation structure distal end 121 less than 0.02 inches or greater than 0.06 inches relative to actuation structure proximal end 122. In one or more embodiments, a compression of actuation structure 120 may be configured to increase a distance between actuation structure distal end 121 and actuation structure proximal end 122 in a range of 0.5 to 2.5 percent. Illustratively, a compression of actuation structure 120 may be configured to increase a distance between actuation structure distal end 121 and actuation structure proximal end 122 by less than 0.5 percent or greater than 2.5 percent. In one or more embodiments, a compression of actuation structure 120 may be configured to increase a distance between handle distal end 101 and handle proximal end 102. Illustratively, a compression of actuation structure 120 may be configured to extend handle distal end 101 relative to handle proximal end 102. In one or more embodiments, a compression of actuation structure 120 may be configured to expand an extension joint 126 of a particular actuation arm 125 of a plurality of actuation arms 125. Illustratively, an expansion of an extension joint 126 of a particular actuation arm 125 may be configured to extend the particular actuation arm 125, e.g., by increasing a distance between a distal end of the particular actuation arm 125 and a proximal end of the particular actuation arm 125. In one or more embodiments, an expansion of an extension joint 126 of a particular actuation arm 125 may be configured to extend a distal end of the particular arm 125 relative to actuation structure proximal end 122. Illustratively, an expansion of an extension joint 126 of a particular actuation arm 125 may be configured to expand an extension joint 126 of each actuation arm 125 of a plurality of actuation arms 125. In one or more embodiments, an expansion of an extension joint 126 of a particular actuation arm 125 may be configured to extend actuation structure distal end 121 relative to actuation structure proximal end 122. Illustratively, an expansion of an extension joint 126 of a particular actuation arm 125 may be configured to extend handle distal end 101 relative to handle proximal end 102. In one or more embodiments, a compression of actuation structure 120 may be configured to expand a plurality of extension joints 126 of a particular actuation arm 125. Illustratively, an expansion of a plurality of extension joints 126 of a particular actuation arm 125 may be configured to expand a plurality of extension joints 126 of each actuation arm 125 of a plurality of actuation arms. In one or more embodiments, an expansion of a plurality of extension joints 126 of a particular actuation arm 125 may be configured to extend actuation structure distal end 121 relative to actuation structure proximal end 122. Illustratively, an expansion of a plurality of extension joints 126 of a particular actuation arm 125 may be configured to extend handle distal end 101 relative to handle proximal end 102.

In one or more embodiments, a decompression of actuation structure 120 may be configured to decrease a distance between actuation structure distal end 121 and actuation structure proximal end 122. Illustratively, a decompression of actuation structure 120 may be configured to retract actuation structure distal end 121 relative to actuation structure proximal end 122. In one or more embodiments, a removal of a force having a magnitude in a range of 0.6 to 1.6 pounds from a portion of actuation structure 120 may be configured to decompress actuation structure 120, e.g., a removal of a force having a magnitude of 1.1 pounds from a portion of actuation structure 120 may be configured to decompress actuation structure 120. Illustratively, a removal of a force having a magnitude less than 0.6 pounds or greater than 1.6 pounds from a portion of actuation structure 120 may be configured to decompress actuation structure 120. In one or more embodiments, a decompression of actuation structure 120 may be configured to retract actuation structure distal end 121 in a range of 0.02 to 0.06 inches relative to actuation structure proximal end 122. Illustratively, a decompression of actuation structure 120 may be configured to retract actuation structure distal end 121 less than 0.02 inches or greater than 0.06 inches relative to actuation structure proximal end 122. In one or more embodiments, a decompression of actuation structure 120 may be configured to decrease a distance between actuation structure distal end 121 and actuation structure proximal end 122 in a range of 0.5 to 2.5 percent. Illustratively, a decompression of actuation structure 120 may be configured to decrease a distance between actuation structure distal end 121 and actuation structure proximal end 122 by less than 0.5 percent or greater than 2.5 percent. In one or more embodiments, a decompression of actuation structure 120 may be configured to decrease a distance between handle distal end 101 and handle proximal end 102. Illustratively, a decompression of actuation structure 120 may be configured to retract handle distal end 101 relative to handle proximal end 102. In one or more embodiments, a decompression of actuation structure 120 may be configured to collapse an extension joint 126 of a particular actuation arm 125 of a plurality of actuation arms 125. Illustratively, a collapse of an extension joint 126 of a particular actuation arm 125 may be configured to retract the particular actuation arm 125, e.g., by decreasing a distance between a distal end of the particular actuation arm 125 and a proximal end of the particular actuation arm 125. In one or more embodiments, a collapse of an extension joint 126 of a particular actuation arm 125 may be configured to retract a distal end of the particular arm 125 relative to actuation structure proximal end 122. Illustratively, a collapse of an extension joint 126 of a particular actuation arm 125 may be configured to collapse an extension joint 126 of each actuation arm 125 of a plurality of actuation arms 125. In one or more embodiments, a collapse of an extension joint 126 of a particular actuation arm 125 may be configured to retract actuation structure distal end 121 relative to actuation structure proximal end 122. Illustratively, a collapse of an extension joint 126 of a particular actuation arm 125 may be configured to retract handle distal end 101 relative to handle proximal end 102. In one or more embodiments, a decompression of actuation structure 120 may be configured to collapse a plurality of extension joints 126 of a particular actuation arm 125. Illustratively, a collapse of a plurality of extension joints 126 of a particular actuation arm 125 may be configured to collapse a plurality of extension joints 126 of each actuation arm 125 of a plurality of actuation arms. In one or more embodiments, a collapse of a plurality of extension joints 126 of a particular actuation arm 125 may be configured to retract actuation structure distal end 121 relative to actuation structure proximal end 122. Illustratively, a collapse of a plurality of extension joints 126 of a particular actuation arm 125 may be configured to retract handle distal end 101 relative to handle proximal end 102.

In one or more embodiments, actuation structure 120 may be manufactured from any suitable material, e.g., polymers, metals, metal alloys, etc., or from any combination of suitable materials. Illustratively, actuation structure 120 may be manufactured from a shape memory material. In one or more embodiments, actuation structure 120 may be manufactured using a selective laser sintering machine. Illustratively, actuation structure 100 may be manufactured by additive manufacturing or 3D printing. In one or more embodiments, actuation structure 120 may be manufactured from a material suitable for sterilization by a medical autoclave. Illustratively, actuation structure 120 may be manufactured from a material, e.g., Nylon, configured to withstand exposure to temperatures, pressures, and ambient conditions present in a medical autoclave without degradation. For example, actuation structure 120 may be configured to function normally after exposure in a temperature 250° F. for 15 minutes at an atmospheric pressure of 15 psi. In one or more embodiments, actuation structure 120 may be configured to be used in a surgical procedure and then sterilized by a medical autoclave at least three times. Illustratively, actuation structure 120 may be configured to be used in a surgical procedure and then sterilized by a medical autoclave more than three times.

In one or more embodiments, actuation structure 120 may have a density in a range of 0.02 to 0.06 pounds per cubic inch, e.g., actuation structure 120 may have a density of 0.041 pounds per cubic inch. Illustratively, actuation structure 120 may have a density less than 0.02 pounds per cubic inch or greater than 0.06 pounds per cubic inch. In one or more embodiments, actuation structure 120 may have a mass in a range of 0.01 to 0.03 pounds, e.g., actuation structure 120 may have a mass of 0.024 pounds. Illustratively, actuation structure 120 may have a mass less than 0.01 pounds or greater than 0.03 pounds. In one or more embodiments, actuation structure 120 may have a volume in a range of 0.3 to 0.7 cubic inches, e.g., actuation structure 120 may have a volume of 0.577 cubic inches. Illustratively, actuation structure 120 may have a volume less than 0.3 cubic inches or greater than 0.7 cubic inches. In one or more embodiments, actuation structure 120 may have a surface area in a range of 10.0 to 20.0 square inches, e.g., actuation structure 120 may have a surface area of 14.87 square inches. Illustratively, actuation structure 120 may have a surface area less than 10.0 square inches or greater than 20.0 square inches.

FIG. 1B illustrates a cross-sectional view of a handle 100. Illustratively, handle 100 may comprise an inner bore 140, an optic fiber housing 145, and a housing tube housing 150. In one or more embodiments, handle 100 may be manufactured from any suitable material, e.g., polymers, metals, metal alloys, etc., or from any combination of suitable materials.

FIGS. 2A, 2B, and 2C are schematic diagrams illustrating a housing tube 200. In one or more embodiments, housing tube 200 may comprise a housing tube distal end 201 and a housing tube proximal end 202. Housing tube 200 may be manufactured from any suitable material, e.g., polymers, metals, metal alloys, etc., or from any combination of suitable materials. Illustratively, housing tube 200 may be manufactured with dimensions configured for microsurgical procedures, e.g., ophthalmic surgical procedures. FIG. 2A illustrates a housing tube 200 oriented to illustrate a first housing tube portion 220. Illustratively, first housing tube portion 220 may have a first stiffness. FIG. 2B illustrates a housing tube 200 oriented to illustrate a second housing tube portion 230. Illustratively, second housing tube portion 230 may have a second stiffness. In one or more embodiments, the second stiffness may be greater than the first stiffness. Illustratively, first housing tube portion 220 may comprise a first material having a first stiffness. In one or more embodiments, second housing tube portion 230 may comprise a second material having a second stiffness. Illustratively, the second stiffness may be greater than the first stiffness.

In one or more embodiments, housing tube 200 may comprise a non-uniform inner diameter or a non-uniform outer diameter, e.g., to vary a stiffness of one or more portions of housing tube 200. Illustratively, a first housing tube portion 220 may comprise a first inner diameter of housing tube 200 and a second housing tube portion 230 may comprise a second inner diameter of housing tube 200. In one or more embodiments, the first inner diameter of housing tube 200 may be larger than the second inner diameter of housing tube 200. Illustratively, a first housing tube portion 220 may comprise a first outer diameter of housing tube 200 and a second housing tube portion 230 may comprise a second outer diameter of housing tube 200. In one or more embodiments, the first outer diameter of housing tube 200 may be smaller than the second outer diameter of housing tube 200.

In one or more embodiments, first housing tube portion 220 may comprise one or more apertures configured to produce a first stiffness of first housing tube portion 220. Illustratively, second housing tube portion 230 may comprise a solid portion of housing tube 200 having a second stiffness. In one or more embodiments, the second stiffness may be greater than the first stiffness. Illustratively, first housing tube portion 220 may comprise one or more apertures configured to produce a first stiffness of first housing tube portion 220. In one or more embodiments, second housing tube portion 230 may comprise one or more apertures configured to produce a second stiffness of second housing tube portion 230. Illustratively, the second stiffness may be greater than the first stiffness.

In one or more embodiments, first housing tube portion 220 may comprise a plurality of slits configured to separate one or more solid portions of housing tube 200. Illustratively, a plurality of slits may be cut, e.g., laser cut, into first housing tube portion 220. In one or more embodiments, first housing tube portion 220 may comprise a plurality of slits configured to minimize a force of friction between housing tube 200 and a cannula, e.g., as housing tube 200 is inserted into the cannula or as housing tube 200 is extracted from the cannula. For example, each slit of the plurality of slits may comprise one or more arches configured to minimize a force of friction between housing tube 200 and a cannula.

FIG. 2C illustrates an angled view of housing tube 200. Illustratively, an optic fiber 210 may be disposed within housing tube 200. In one or more embodiments, optic fiber 210 may comprise an optic fiber distal end 211 and an optic fiber proximal end 212. Illustratively, optic fiber 210 may be configured to transmit light, e.g., laser light, illumination light, etc. In one or more embodiments, optic fiber 210 may be disposed within housing tube 200 wherein optic fiber distal end 211 may be adjacent to housing tube distal end 201. Illustratively, optic fiber 210 may be disposed within housing tube 200 wherein a portion of optic fiber 210 may be adjacent to a portion of first housing tube portion 220. In one or more embodiments, a portion of optic fiber 210 may be fixed to an inner portion of housing tube 200, e.g., by an adhesive or any suitable fixation means.

FIG. 3 is a schematic diagram illustrating an exploded view of a steerable laser probe assembly 300. In one or more embodiments, a steerable laser probe assembly 300 may comprise a handle 100, a housing tube 200 having a housing tube distal end 201 and a housing tube proximal end 202, an optic fiber 210 having an optic fiber distal end 211 and an optic fiber proximal end 212, a fixation mechanism 310, and a light source interface 320. Illustratively, light source interface 320 may be configured to interface with optic fiber 210, e.g., at optic fiber proximal end 212. In one or more embodiments, light source interface 320 may comprise a standard light source connecter, e.g., an SMA connector.

Illustratively, a portion of housing tube 200 may be fixed to a portion of handle 100, e.g., housing tube proximal end 202 may be fixed to handle distal end 101. In one or more embodiments, a portion of housing tube 200 may be fixed to a portion of handle 100, e.g., by an adhesive or any suitable fixation means. Illustratively, a portion of housing tube 200 may be disposed within housing tube housing 150, e.g., housing tube proximal end 202 may be disposed within housing tube housing 150. In one or more embodiments, a portion of housing tube 200 may be fixed within housing tube housing 150, e.g., by an adhesive or any suitable fixation means. For example, housing tube 200 may be fixed within housing tube housing 150 by a press fit, a weld, a setscrew, etc.

Illustratively, optic fiber 210 may be disposed within inner bore 140, optic fiber housing 145, housing tube housing 150, and housing tube 200. In one or more embodiments, optic fiber 210 may be disposed within housing tube 200 wherein optic fiber distal end 211 may be adjacent to housing tube distal end 201. Illustratively, optic fiber 210 may be disposed within housing tube 200 wherein a portion of optic fiber 210 may be adjacent to a portion of first housing tube portion 220. In one or more embodiments, a portion of optic fiber 210 may be fixed to a portion of housing tube 200, e.g., by an adhesive or any suitable fixation means. Illustratively, a portion of optic fiber 210 may be fixed within optic fiber housing 145, e.g., by an adhesive or any suitable fixation means. In one or more embodiments, fixation mechanism 310 may be configured to fix a portion of optic fiber 210 within optic fiber housing 145, e.g., fixation mechanism 310 may be disposed within fixation mechanism housing 115 and optic fiber housing 145. Illustratively, fixation mechanism 310 may be configured to fix a portion of optic fiber 210 within optic fiber housing 145, e.g., by a press fit or any suitable fixation means. In one or more embodiments, fixation mechanism 310 may comprise a set screw, e.g., configured to fix a portion of optic fiber 210 within optic fiber housing 145.

Illustratively, a compression of actuation structure 120 may be configured to extend actuation structure distal end 121 relative to actuation structure proximal end 122. In one or more embodiments, an extension of actuation structure distal end 121 relative to actuation structure proximal end 122 may be configured to extend handle distal end 101 relative to handle proximal end 102. Illustratively, an extension of handle distal end 101 relative to handle proximal end 102 may be configured to extend housing tube 200 relative to handle proximal end 102. In one or more embodiments, an extension of housing tube 200 relative to handle proximal end 102 may be configured to extend housing tube 200 relative to optic fiber 210. Illustratively, a portion of optic fiber 210, e.g., a portion of optic fiber 210 fixed to housing tube 200, may be configured to resist an extension of housing tube 200 relative to optic fiber 210. In one or more embodiments, an extension of housing tube 200 relative to optic fiber 210 may be configured to compress a portion of housing tube 200, e.g., a portion of optic fiber 210 fixed to a portion of housing tube 200 may be configured compress a portion of housing tube 200. Illustratively, a compression of a portion of housing tube 200, e.g., first housing tube portion 220, may be configured to cause housing tube 200 to gradually curve. In one or more embodiments, a gradual curving of housing tube 200 may be configured to gradually curve optic fiber 210. Illustratively, a compression of actuation structure 120 may be configured to gradually curve housing tube 200. In one or more embodiments, a compression of actuation structure 120 may be configured to gradually curve optic fiber 210.

Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract handle distal end 101 relative to handle proximal end 102. Illustratively, a retraction of handle distal end 101 relative to handle proximal end 102 may be configured to retract housing tube 200 relative to handle proximal end 102. In one or more embodiments, a retraction of housing tube 200 relative to handle proximal end 102 may be configured to retract housing tube 200 relative to optic fiber 210. Illustratively, a portion of optic fiber 210, e.g., a portion of optic fiber 210 fixed to housing tube 200, may be configured to facilitate a retraction of housing tube 200 relative to optic fiber 210. In one or more embodiments, a retraction of housing tube 200 relative to optic fiber 210 may be configured to decompress a portion of housing tube 200, e.g., a portion of optic fiber 210 fixed to a portion of housing tube 200 may be configured decompress a portion of housing tube 200. Illustratively, a decompression of a portion of housing tube 200, e.g., first housing tube portion 220, may be configured to cause housing tube 200 to gradually straighten. In one or more embodiments, a gradual straightening of housing tube 200 may be configured to gradually straighten optic fiber 210. Illustratively, a decompression of actuation structure 120 may be configured to gradually straighten housing tube 200. In one or more embodiments, a decompression of actuation structure 120 may be configured to gradually straighten optic fiber 210.

Figure 4A:
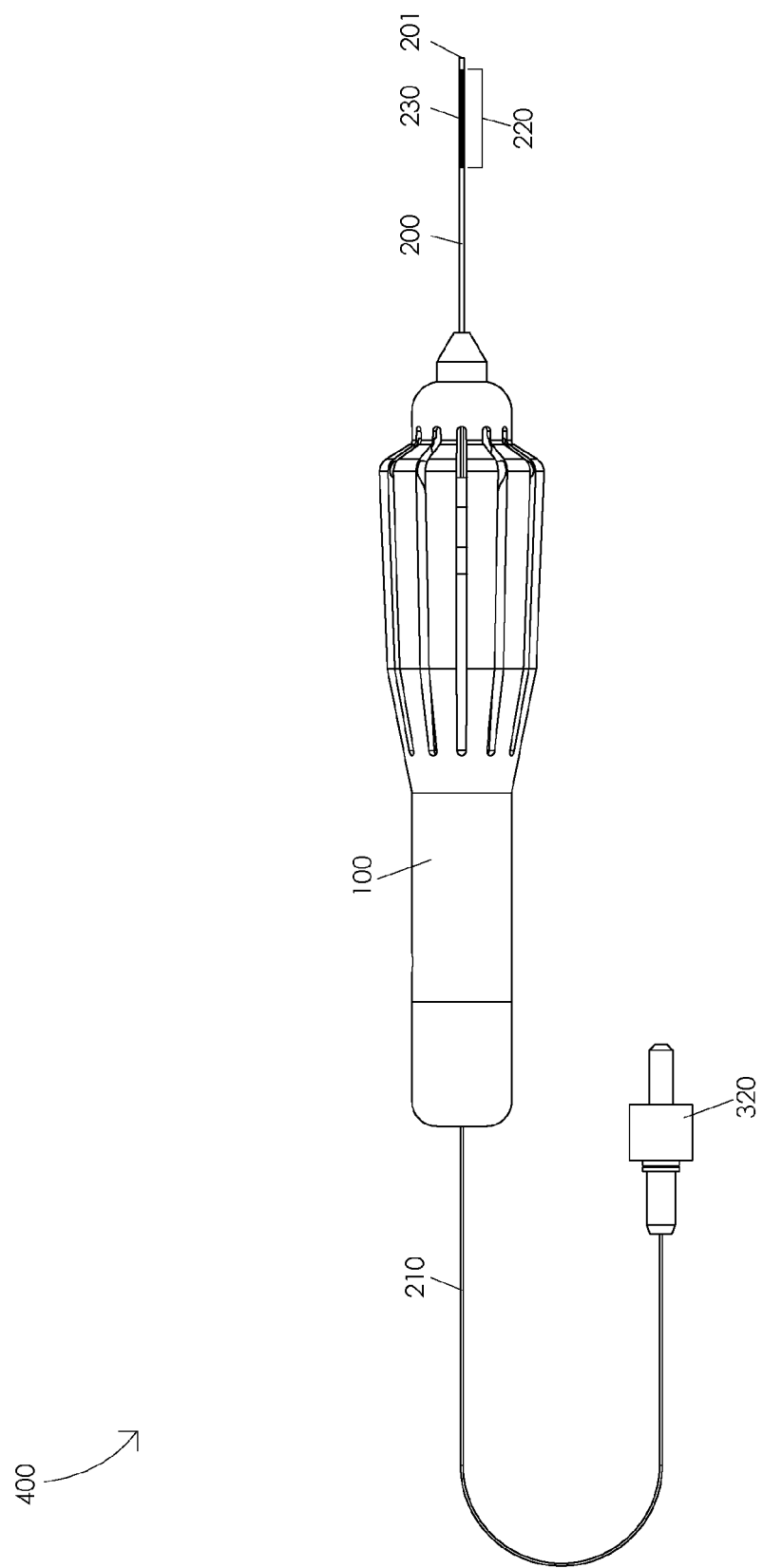

FIGS. 4A, 4B, 4C, 4D, and 4E are schematic diagrams illustrating a gradual curving of an optic fiber 210. FIG. 4A illustrates a straight optic fiber 400. In one or more embodiments, optic fiber 210 may comprise a straight optic fiber 400, e.g., when actuation structure 120 is fully decompressed. Illustratively, optic fiber 210 may comprise a straight optic fiber 400, e.g., when housing tube 200 is fully retracted relative to optic fiber 210. For example, optic fiber 210 may comprise a straight optic fiber 400, e.g., when first housing tube portion 220 is fully decompressed. Illustratively, a line tangent to optic fiber distal end 211 may be parallel to a line tangent to housing tube proximal end 202, e.g., when optic fiber 210 comprises a straight optic fiber 400.

FIG. 4B illustrates an optic fiber in a first curved position 410. In one or more embodiments, a compression of actuation structure 120 may be configured to gradually curve optic fiber 210 from a straight optic fiber 400 to an optic fiber in a first curved position 410. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to optic fiber 210. Illustratively, an extension of housing tube 200 relative to optic fiber 210 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from a straight optic fiber 400 to an optic fiber in a first curved position 410. In one or more embodiments, a line tangent to optic fiber distal end 211 may intersect a line tangent to housing tube proximal end 202 at a first angle, e.g., when optic fiber 210 comprises an optic fiber in a first curved position 410. In one or more embodiments, the first angle may comprise any angle greater than zero degrees. For example, the first angle may comprise a 45 degree angle.

Figure 4C:
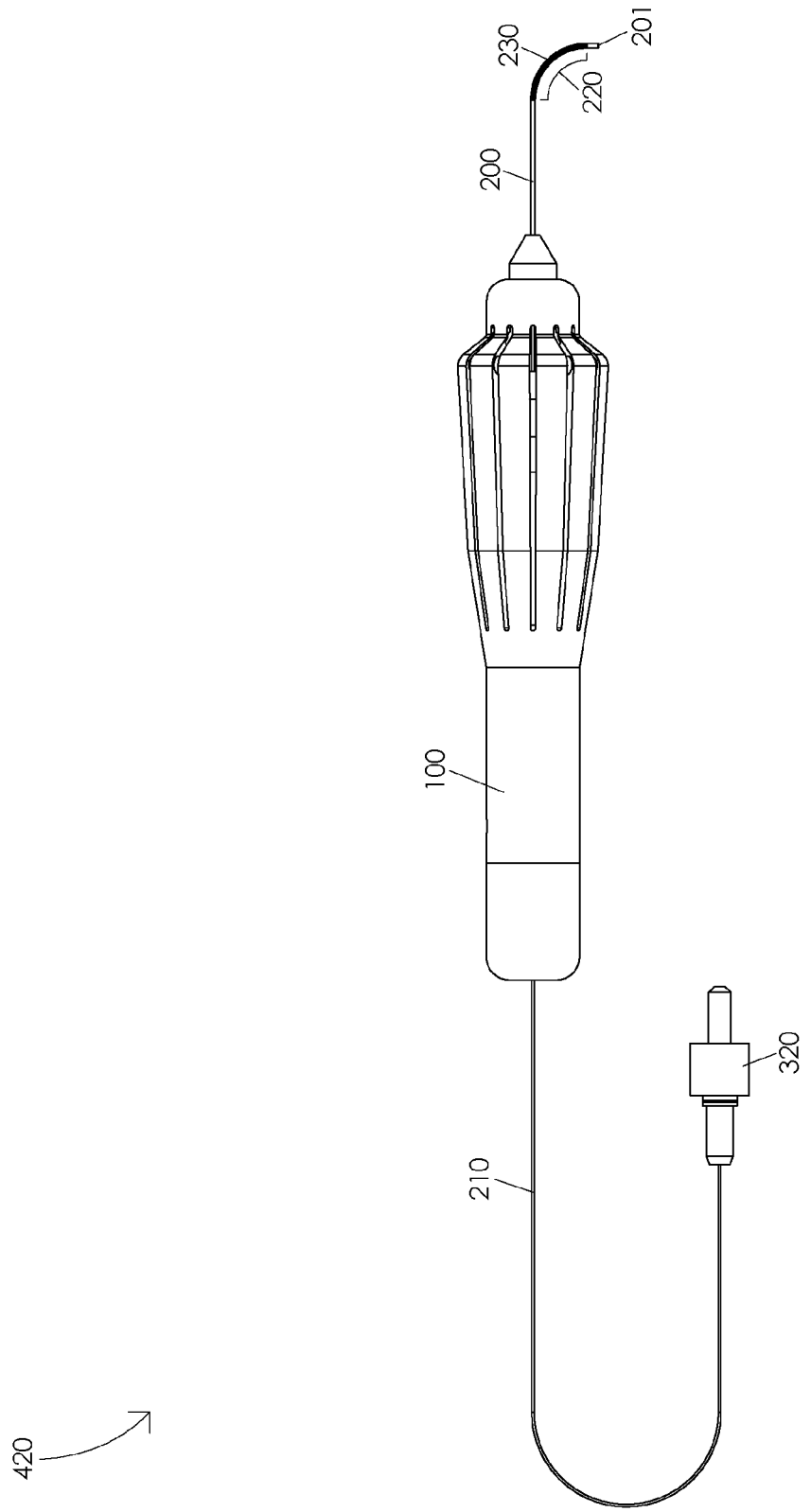

FIG. 4C illustrates an optic fiber in a second curved position 420. In one or more embodiments, a compression of actuation structure 120 may be configured to gradually curve optic fiber 210 from an optic fiber in a first curved position 410 to an optic fiber in a second curved position 420. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to optic fiber 210. Illustratively, an extension of housing tube 200 relative to optic fiber 210 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from an optic fiber in a first curved position 410 to an optic fiber in a second curved position 420. In one or more embodiments, a line tangent to optic fiber distal end 211 may intersect a line tangent to housing tube proximal end 202 at a second angle, e.g., when optic fiber 210 comprises an optic fiber in a second curved position 420. In one or more embodiments, the second angle may comprise any angle greater than the first angle. For example, the second angle may comprise a 90 degree angle.

Figure 4D:
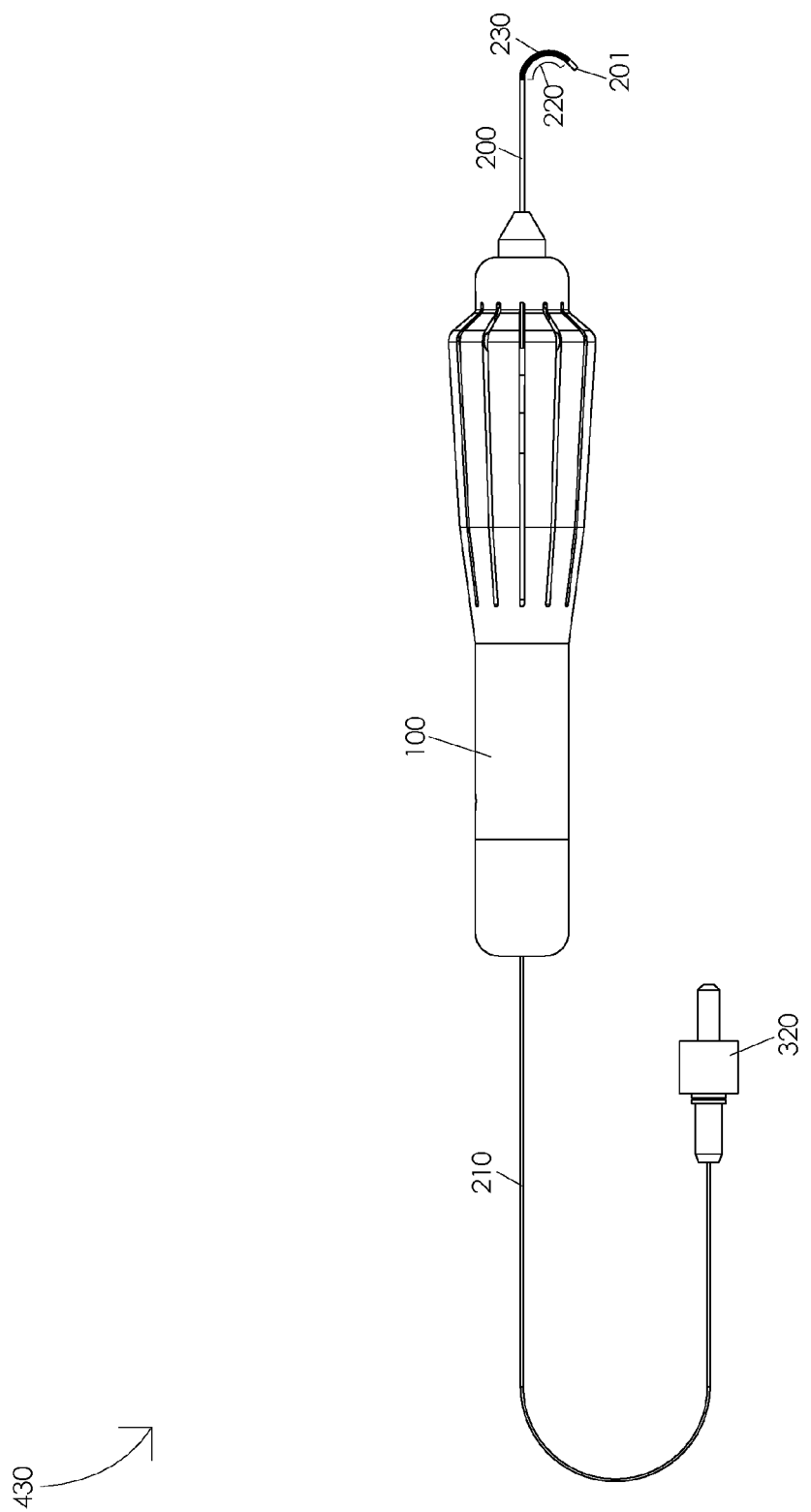

FIG. 4D illustrates an optic fiber in a third curved position 430. In one or more embodiments, a compression of actuation structure 120 may be configured to gradually curve optic fiber 210 from an optic fiber in a second curved position 420 to an optic fiber in a third curved position 430. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to optic fiber 210. Illustratively, an extension of housing tube 200 relative to optic fiber 210 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from an optic fiber in a second curved position 420 to an optic fiber in a third curved position 430. In one or more embodiments, a line tangent to optic fiber distal end 211 may intersect a line tangent to housing tube proximal end 202 at a third angle, e.g., when optic fiber 210 comprises an optic fiber in a third curved position 430. In one or more embodiments, the third angle may comprise any angle greater than the second angle. For example, the third angle may comprise a 135 degree angle.

Figure 4E:
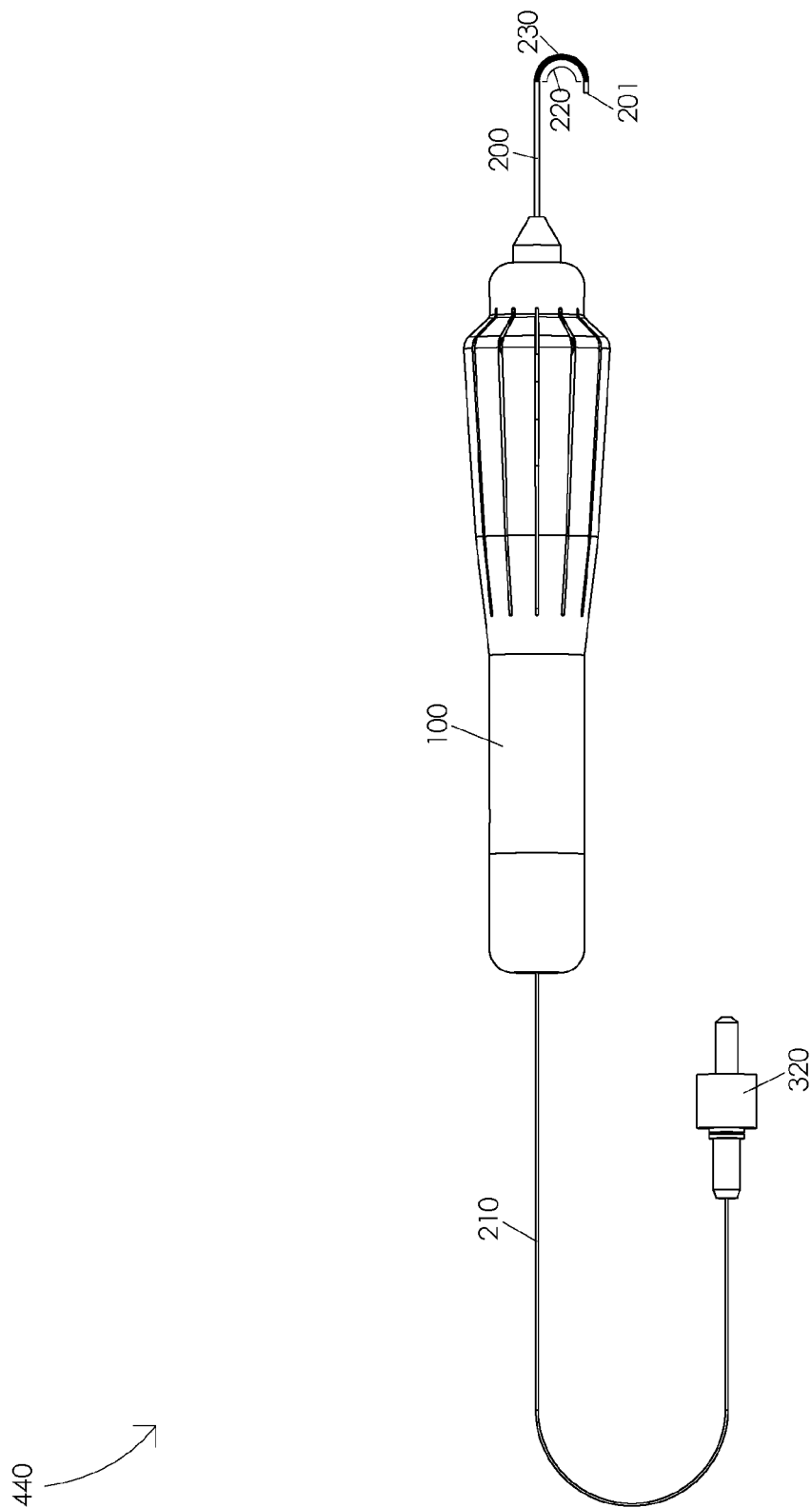

FIG. 4E illustrates an optic fiber in a fourth curved position 440. In one or more embodiments, a compression of actuation structure 120 may be configured to gradually curve optic fiber 210 from an optic fiber in a third curved position 430 to an optic fiber in a fourth curved position 440. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to optic fiber 210. Illustratively, an extension of housing tube 200 relative to optic fiber 210 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from an optic fiber in a third curved position 430 to an optic fiber in a fourth curved position 440. In one or more embodiments, a line tangent to optic fiber distal end 211 may be parallel to a line tangent to housing tube proximal end 202, e.g., when optic fiber 210 comprises an optic fiber in a fourth curved position 440.

In one or more embodiments, one or more properties of a steerable laser probe may be adjusted to attain one or more desired steerable laser probe features. Illustratively, a length that housing tube distal end 201 extends from handle distal end 101 may be adjusted to vary an amount of compression of actuation structure 120 configured to curve housing tube 200 to a particular curved position. In one or more embodiments, a stiffness of first housing tube portion 220 or a stiffness of second housing tube portion 230 may be adjusted to vary an amount of compression of actuation structure 120 configured to curve housing tube 200 to a particular curved position. Illustratively, a material comprising first housing tube portion 220 or a material comprising second housing tube portion 230 may be adjusted to vary an amount of compression of actuation structure 120 configured to curve housing tube 200 to a particular curved position.

In one or more embodiments, a number of apertures in housing tube 200 may be adjusted to vary an amount of compression of actuation structure 120 configured to curve housing tube 200 to a particular curved position. Illustratively, a location of one or more apertures in housing tube 200 may be adjusted to vary an amount of compression of actuation structure 120 configured to curve housing tube 200 to a particular curved position. In one or more embodiments, a geometry of one or more apertures in housing tube 200 may be adjusted to vary an amount of compression of actuation structure 120 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be non-uniform, e.g., a first aperture in housing tube 200 may have a first geometry and a second aperture in housing tube 200 may have a second geometry. Illustratively, a geometry or location of one or more apertures in housing tube 200 may be optimized to evenly distribute an applied force. For example, a geometry or location of one or more apertures in housing tube 200 may be optimized to evenly distribute a compressive force applied to first housing tube portion 220.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position. Illustratively, a geometry of actuation structure 120 may be adjusted to vary an amount of compression of actuation structure 120 configured to curve housing tube 200 to a particular curved position. In one or more embodiments, one or more locations within housing tube 200 wherein optic fiber 210 may be fixed to a portion of housing tube 200 may be adjusted to vary an amount of compression of actuation structure 120 configured to curve housing tube 200 to a particular curved position.

In one or more embodiments, at least a portion of optic fiber 210 may be enclosed in an optic fiber sleeve configured to, e.g., protect optic fiber 210, vary a stiffness of optic fiber 210, vary an optical property of optic fiber 210, etc. Illustratively, an optic fiber sleeve may be configured to compress a portion of housing tube 200, e.g., first housing tube portion 220. In one or more embodiments, a portion of an optic fiber sleeve may be fixed within optic fiber housing 145, e.g., by an adhesive or any suitable fixation means. Illustratively, a portion of an optic fiber sleeve may be fixed to a portion of housing tube 200, e.g., by an adhesive or any suitable fixation means. In one or more embodiments, a compression of actuation structure 120 may be configured to extend housing tube 200 relative to an optic fiber sleeve. Illustratively, a portion of an optic fiber sleeve, e.g., a portion of an optic fiber sleeve fixed to a portion of housing tube 200, may be configured to resist an extension of housing tube 200 relative to the optic fiber sleeve. In one or more embodiments, an extension of housing tube 200 relative to an optic fiber sleeve may be configured to compress a portion of housing tube 200, e.g., first housing tube portion 220. Illustratively, a compression of a portion of housing tube 200 may be configured to gradually curve housing tube 200. In one or more embodiments, a gradual curving of housing tube 200 may be configured to gradually curve optic fiber 210.

Illustratively, optic fiber 210 may comprise a buffer, a cladding disposed in the buffer, and a core disposed in the cladding. In one or more embodiments, at least a portion of optic fiber 210 may comprise a buffer configured to protect an optical property of optic fiber 210. Illustratively, at least a portion of optic fiber 210 may comprise a buffer configured to protect an optical layer of optic fiber 210, e.g., the buffer may protect an optical layer of a curved portion of optic fiber 210. In one or more embodiments, at least a portion of optic fiber 210 may comprise a polyimide buffer configured to protect an optical property of optic fiber 210. For example, at least a portion of optic fiber 210 may comprise a Kapton buffer configured to protect an optical property of optic fiber 210.

Illustratively, a steerable laser probe may be configured to indicate, e.g., to a surgeon, a direction that optic fiber 210 may curve, e.g., due to a compression of actuation structure 120. In one or more embodiments, a portion of a steerable laser probe, e.g., handle 100, may be marked in a manner configured to indicate a direction that optic fiber 210 may curve. For example, a portion of handle 100 may comprise an arrow marking configured to indicate a direction that optic fiber 210 may curve. Illustratively, a portion of housing tube 200 may comprise a mark configured to indicate a direction that optic fiber 210 may curve. In one or more embodiments, housing tube 200 may comprise a slight curve, e.g., a curve less than 7.5 degrees, when actuation structure 120 is fully decompressed. Illustratively, housing tube 200 may comprise a slight curve, e.g., a curve equal to or greater than 7.5 degrees, when actuation structure 120 is fully decompressed. In one or more embodiments, housing tube 200 may comprise a slight curve configured to indicate a direction that optic fiber 210 may curve, e.g., due to a compression of actuation structure 120.

Figure 5A:
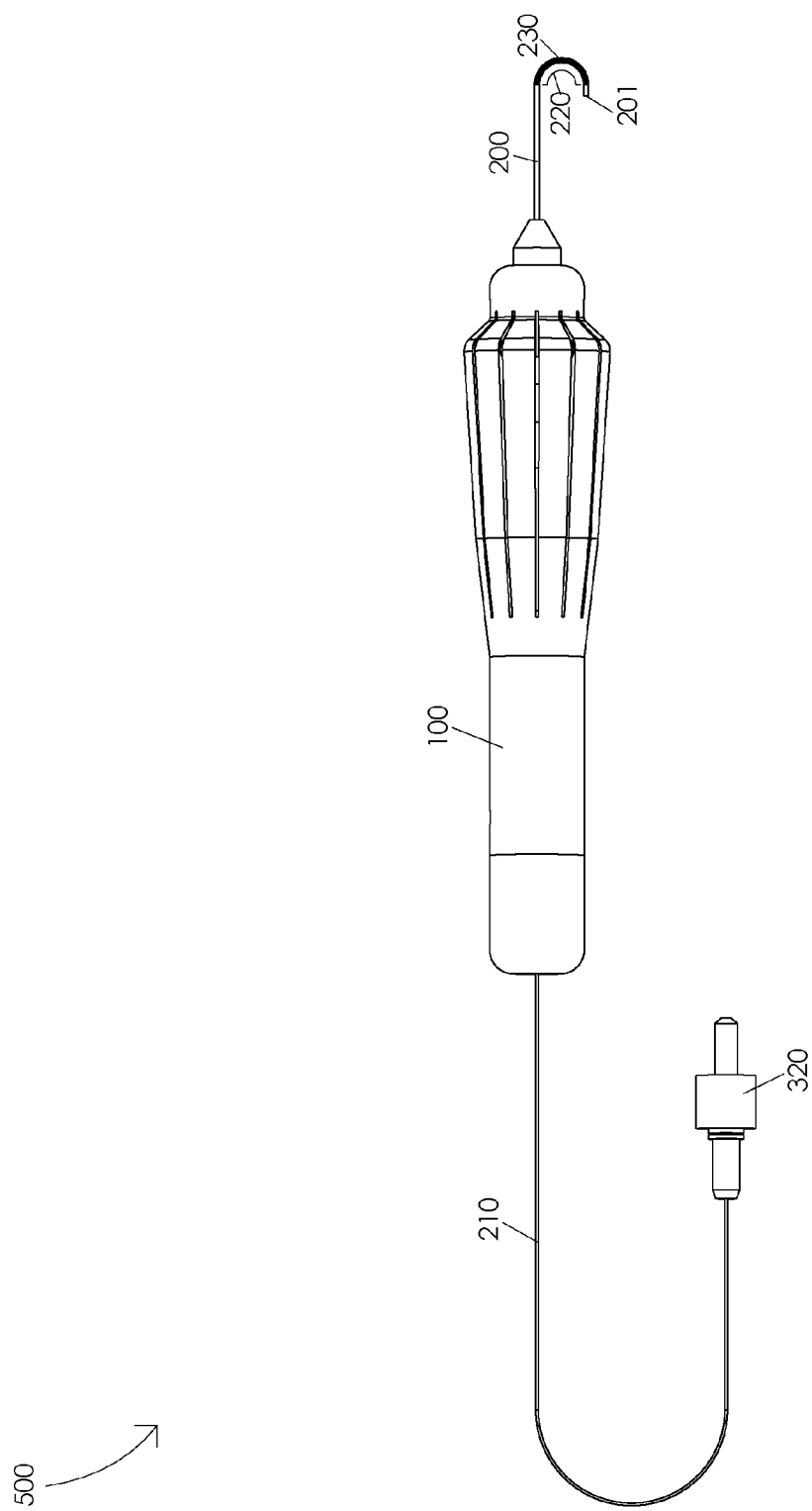
FIGS. 5A, 5B, 5C, 5D, and 5E are schematic diagrams illustrating a gradual straightening of an optic fiber.

FIGS. 5A, 5B, 5C, 5D, and 5E are schematic diagrams illustrating a gradual straightening of an optic fiber 210. FIG. 5A illustrates a fully curved optic fiber 500. In one or more embodiments, optic fiber 210 may comprise a fully curved optic fiber 500, e.g., when actuation structure 120 is fully compressed. Illustratively, optic fiber 210 may comprise a fully curved optic fiber 500, e.g., when housing tube 200 is fully extended relative to optic fiber 210. For example, optic fiber 210 may comprise a fully curved optic fiber 500, e.g., when first housing tube portion 220 is fully compressed. In one or more embodiments, a line tangent to optic fiber distal end 211 may be parallel to a line tangent to housing tube proximal end 202, e.g., when optic fiber 210 comprises a fully curved optic fiber 500.

Figure 5B:
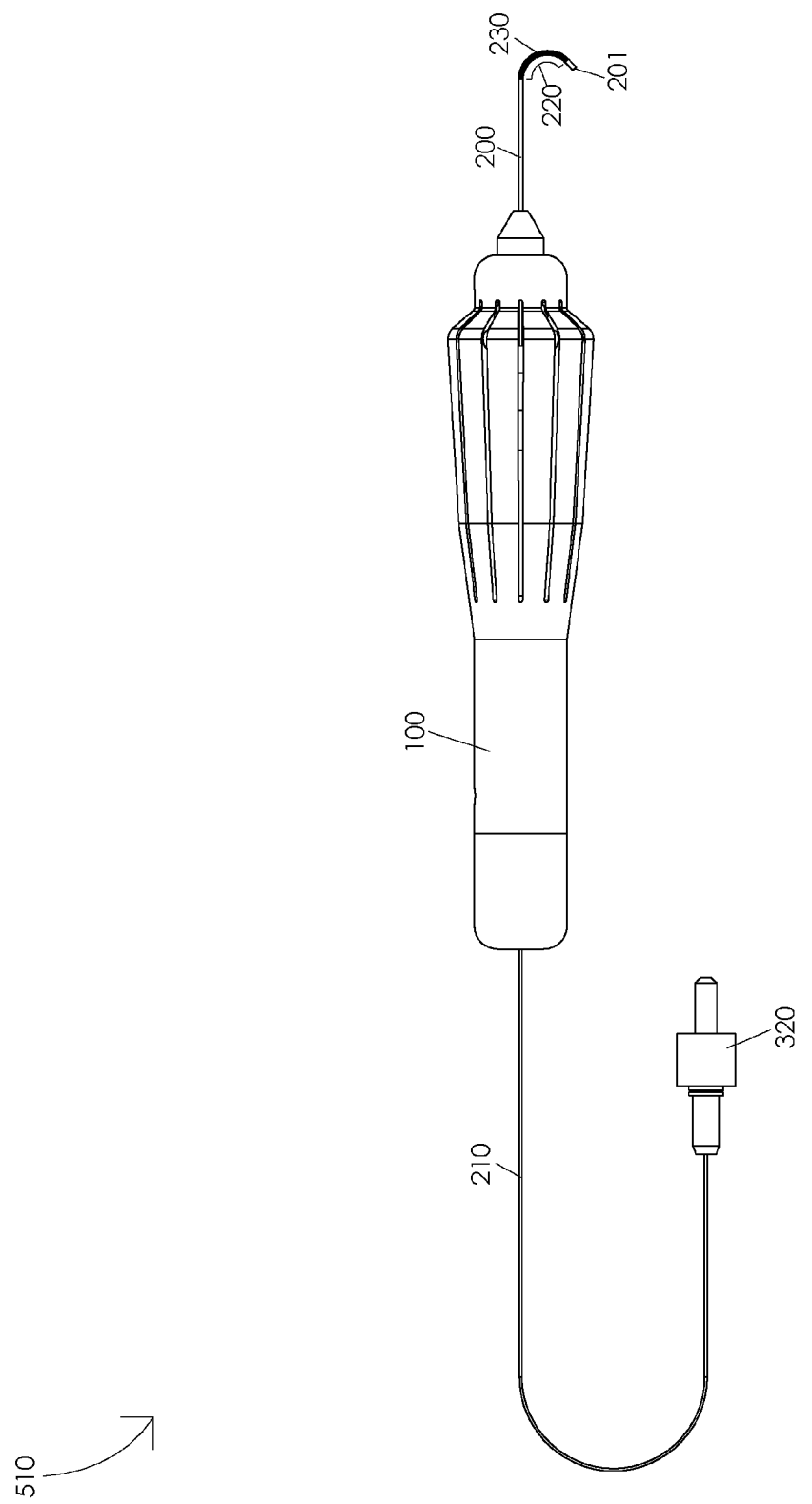

FIG. 5B illustrates an optic fiber in a first partially straightened position 510. In one or more embodiments, a decompression of actuation structure 120 may be configured to gradually straighten optic fiber 210 from a fully curved optic fiber 500 to an optic fiber in a first partially straightened position 510. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract housing tube 200 relative to optic fiber 210. Illustratively, a portion of optic fiber 210, e.g., a portion of optic fiber 210 fixed to a portion of housing tube 200, may be configured to facilitate a retraction of housing tube 200 relative to optic fiber 210. In one or more embodiments, a retraction of housing tube 200 relative to optic fiber 210 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from a fully curved optic fiber 500 to an optic fiber in a first partially straightened position 510. Illustratively, a line tangent to optic fiber distal end 211 may intersect a line tangent to housing tube proximal end 202 at a first partially straightened angle, e.g., when optic fiber 210 comprises an optic fiber in a first partially straightened position 510. In one or more embodiments, the first partially straightened angle may comprise any angle less than 180 degrees. For example, the first partially straightened angle may comprise a 135 degree angle.

Figure 5C:
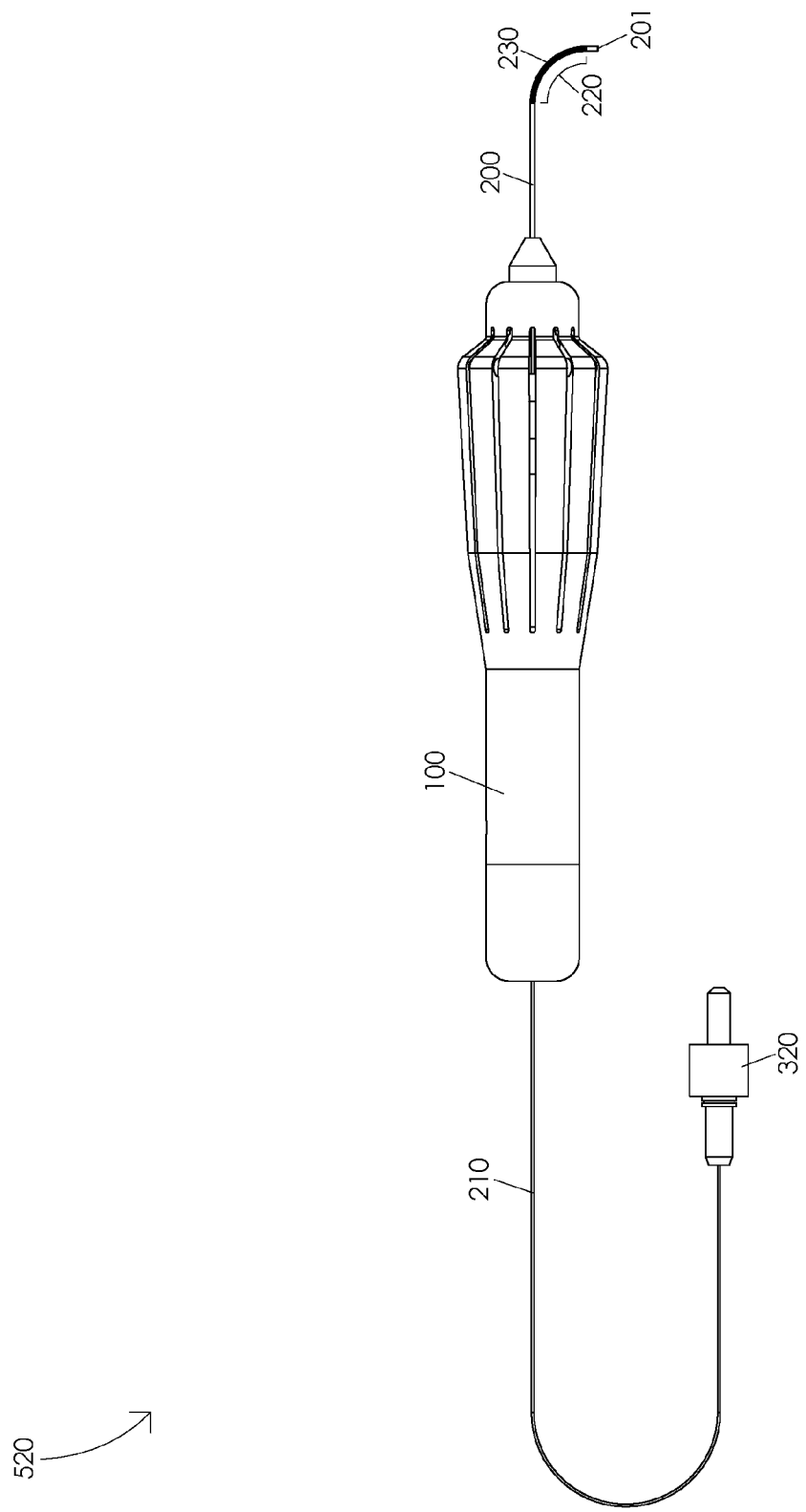

FIG. 5C illustrates an optic fiber in a second partially straightened position 520. In one or more embodiments, a decompression of actuation structure 120 may be configured to gradually straighten optic fiber 210 from an optic fiber in a first partially straightened position 510 to an optic fiber in a second partially straightened position 520. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract housing tube 200 relative to optic fiber 210. Illustratively, a portion of optic fiber 210, e.g., a portion of optic fiber 210 fixed to a portion of housing tube 200, may be configured to facilitate a retraction of housing tube 200 relative to optic fiber 210. In one or more embodiments, a retraction of housing tube 200 relative to optic fiber 210 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from an optic fiber in a first partially straightened position 510 to an optic fiber in a second partially straightened position 520. Illustratively, a line tangent to optic fiber distal end 211 may intersect a line tangent to housing tube proximal end 202 at a second partially straightened angle, e.g., when optic fiber 210 comprises an optic fiber in a second partially straightened position 520. In one or more embodiments, the second partially straightened angle may comprise any angle less than the first partially straightened angle. For example, the second partially straightened angle may comprise a 90 degree angle.

Figure 5D:
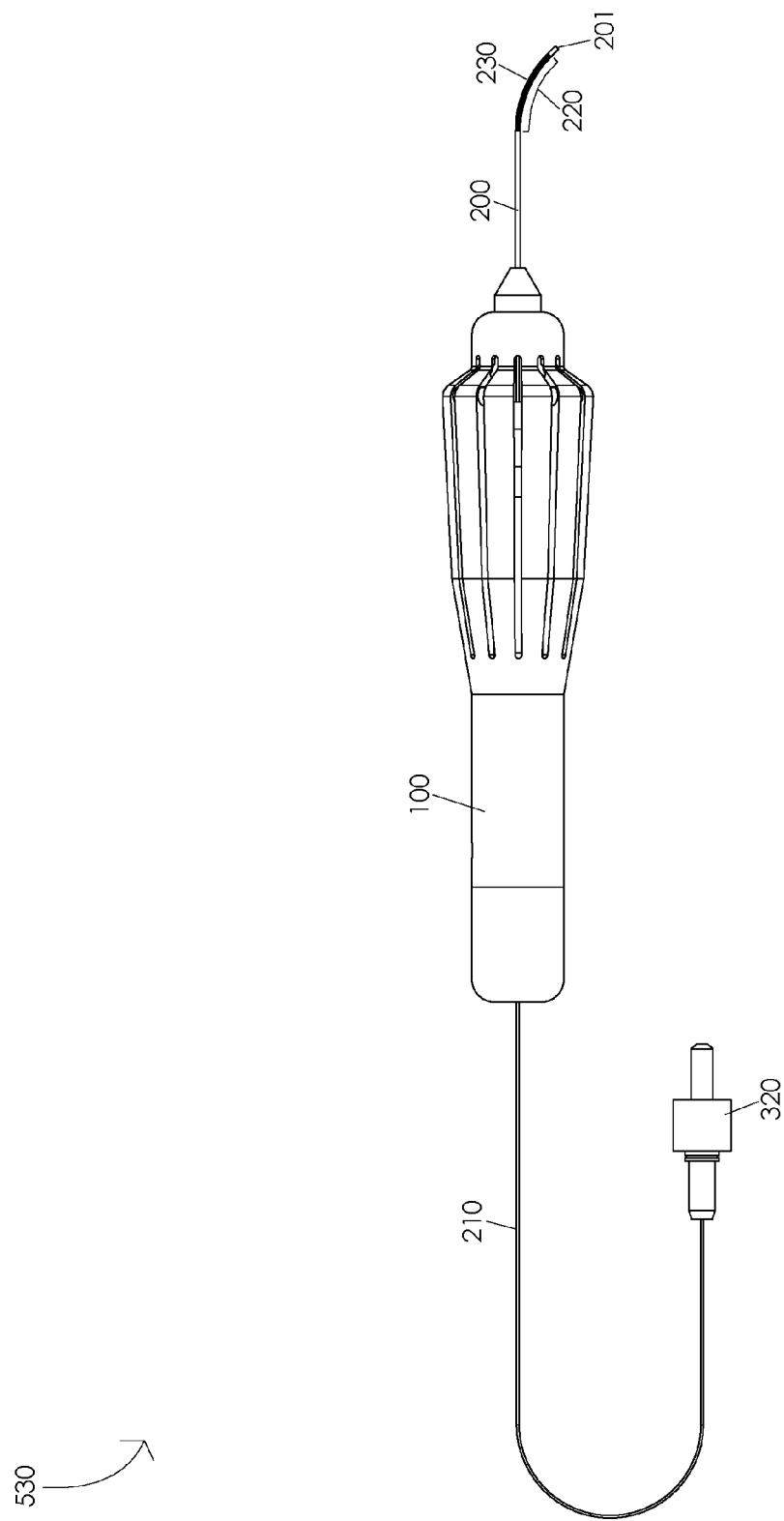

FIG. 5D illustrates an optic fiber in a third partially straightened position 530. In one or more embodiments, a decompression of actuation structure 120 may be configured to gradually straighten optic fiber 210 from an optic fiber in a second partially straight-ended position 520 to an optic fiber in a third partially straightened position 530. Illustratively, a decompression of actuation structure 120 may be configured to retract actuation structure distal end 121 relative to actuation structure proximal end 122. In one or more embodiments, a refraction of actuation structure distal end 121 relative to actuation structure proximal end 122 may be configured to retract housing tube 200 relative to optic fiber 210. Illustratively, a portion of optic fiber 210, e.g., a portion of optic fiber 210 fixed to a portion of housing tube 200, may be configured to facilitate a retraction of housing tube 200 relative to optic fiber 210. In one or more embodiments, a retraction of housing tube 200 relative to optic fiber 210 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from an optic fiber in a second partially straightened position 520 to an optic fiber in a third partially straightened position 530. Illustratively, a line tangent to optic fiber distal end 211 may intersect a line tangent to housing tube proximal end 202 at a third partially straightened angle, e.g., when optic fiber 210 comprises an optic fiber in a third partially straightened position 530. In one or more embodiments, the third partially straightened angle may comprise any angle less than the second partially straightened angle. For example, the third partially straightened angle may comprise a 45 degree angle.

Figure 5E:
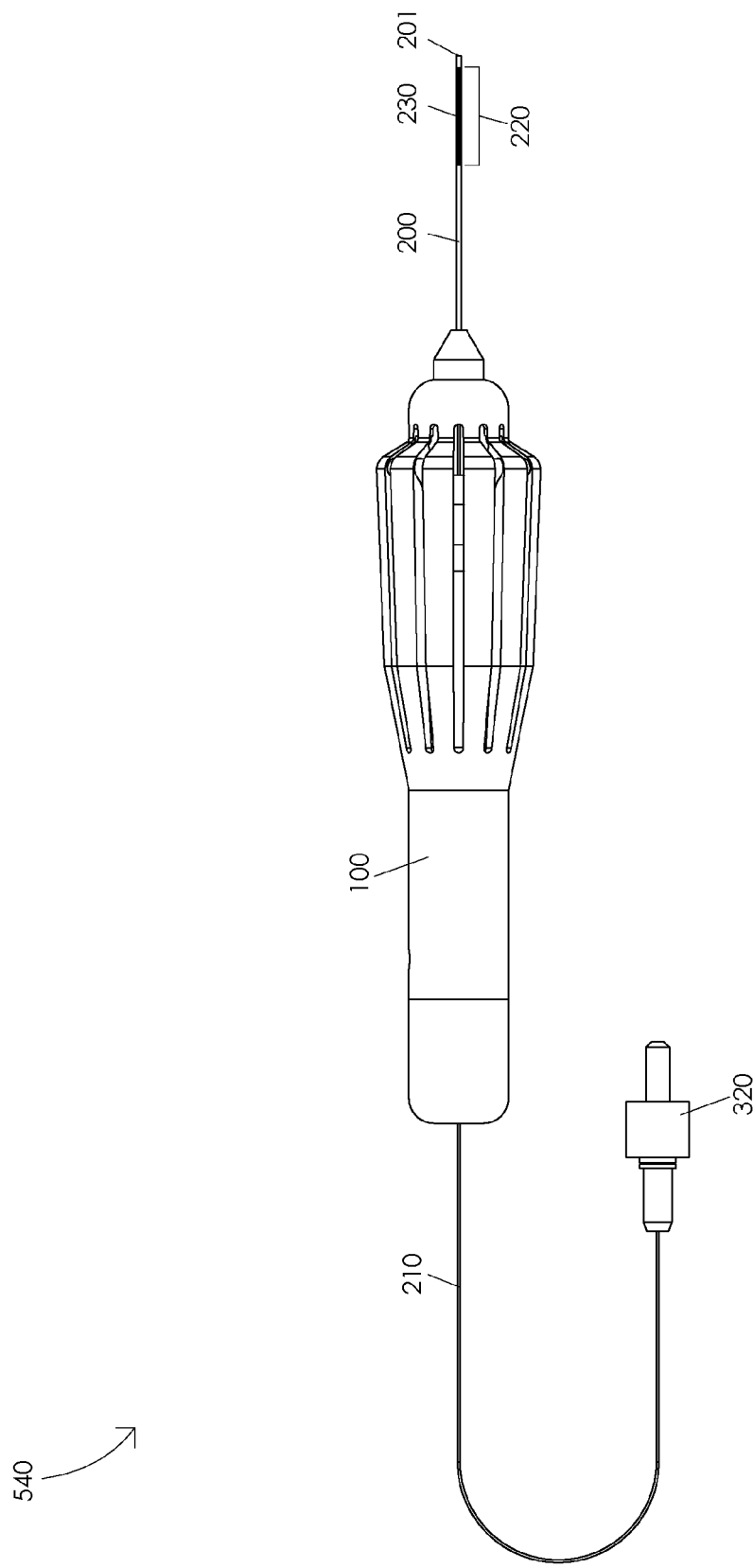

FIG. 5E illustrates an optic fiber in a fully straightened position 540. In one or more embodiments, a decompression of actuation structure 120 may be configured to gradually straighten optic fiber 210 from an optic fiber in a third partially straightened position 530 to an optic fiber in a fully straightened position 540. Illustratively, a decompression of actuation structure 120 may be configured to retract actuation structure distal end 121 relative to actuation structure proximal end 122. In one or more embodiments, a refraction of actuation structure distal end 121 relative to actuation structure proximal end 122 may be configured to retract housing tube 200 relative to optic fiber 210. Illustratively, a portion of optic fiber 210, e.g., a portion of optic fiber 210 fixed to a portion of housing tube 200, may be configured to facilitate a retraction of housing tube 200 relative to optic fiber 210. In one or more embodiments, a retraction of housing tube 200 relative to optic fiber 210 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from an optic fiber in a third partially straightened position 530 to an optic fiber in a fully straightened position 540. Illustratively, a line tangent to optic fiber distal end 211 may be parallel to a line tangent to housing tube proximal end 202, e.g., when optic fiber 210 comprises an optic fiber in a fully straightened position 540.

Illustratively, a surgeon may aim optic fiber distal end 211 at any of a plurality of targets within an eye, e.g., to perform a photocoagulation procedure, to illuminate a surgical target site, etc. In one or more embodiments, a surgeon may aim optic fiber distal end 211 at any target within a particular transverse plane of the inner eye by, e.g., rotating handle 100 to orient housing tube 200 in an orientation configured to cause a curvature of housing tube 200 within the particular transverse plane of the inner eye and varying an amount of compression of actuation structure 120. Illustratively, a surgeon may aim optic fiber distal end 211 at any target within a particular sagittal plane of the inner eye by, e.g., rotating handle 100 to orient housing tube 200 in an orientation configured to cause a curvature of housing tube 200 within the particular sagittal plane of the inner eye and varying an amount of compression of actuation structure 120. In one or more embodiments, a surgeon may aim optic fiber distal end 211 at any target within a particular frontal plane of the inner eye by, e.g., varying an amount of compression of actuation structure 120 to orient a line tangent to optic fiber distal end 211 wherein the line tangent to optic fiber distal end 211 is within the particular frontal plane of the inner eye and rotating handle 100. Illustratively, a surgeon may aim optic fiber distal end 211 at any target located outside of the particular transverse plane, the particular sagittal plane, and the particular frontal plane of the inner eye, e.g., by varying a rotational orientation of handle 100 and varying an amount of compression of actuation structure 120. In one or more embodiments, a surgeon may aim optic fiber distal end 211 at any target of a plurality of targets within an eye, e.g., without increasing a length of a portion of a steerable laser probe within the eye. Illustratively, a surgeon may aim optic fiber distal end 211 at any target of a plurality of targets within an eye, e.g., without decreasing a length of a portion of a steerable laser probe within the eye.

FIGS. 6A and 6B are schematic diagrams illustrating a handle 600. FIG. 6A illustrates a top view of a handle 600. Illustratively, handle 600 may comprise a handle distal end 601, a handle proximal end 602, a handle end plug 610, a fixation mechanism housing 615, and an actuation structure 120 having an actuation structure distal end 121 and an actuation structure proximal end 122. In one or more embodiments, actuation structure 120 may comprise a plurality of actuation arms 125. Illustratively, each actuation arm 125 of a plurality of actuation arms 125 may comprise one or more extension joints 126. FIG. 6B illustrates a cross-sectional view of a handle 600. Illustratively, handle 600 may comprise an inner bore 640, a cable housing 645, and a housing tube housing 650. In one or more embodiments, handle 600 may be manufactured from any suitable material, e.g., polymers, metals, metal alloys, etc., or from any combination of suitable materials.

Figure 7:
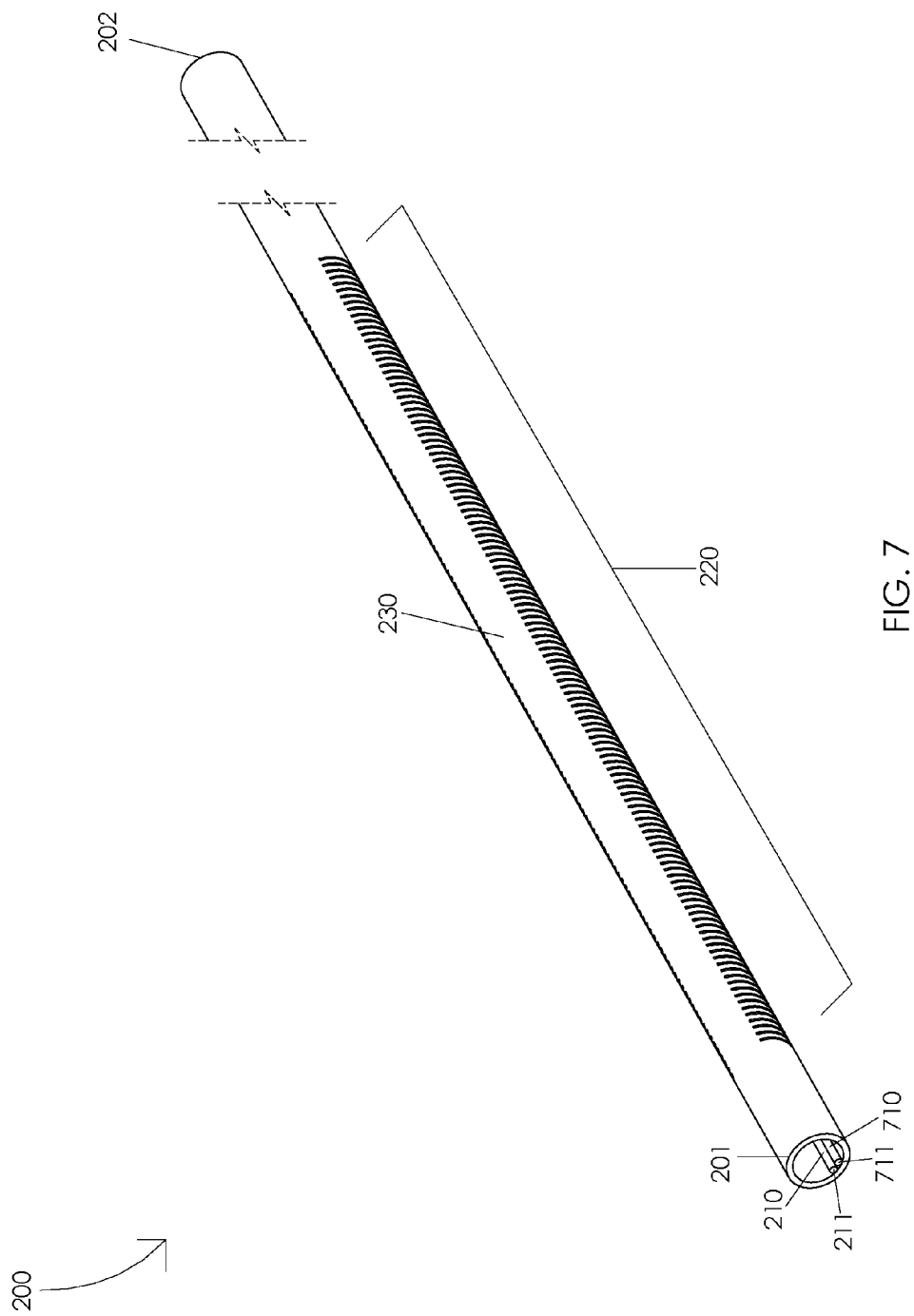
FIG. 7 is a schematic diagram illustrating a housing tube.

FIG. 7 is a schematic diagram illustrating a housing tube 200. Illustratively, an optic fiber 210 may be disposed within housing tube 200. In one or more embodiments, optic fiber 210 may comprise an optic fiber distal end 211 and an optic fiber proximal end 212. Illustratively, optic fiber 210 may be configured to transmit light, e.g., laser light, illumination light, etc. In one or more embodiments, optic fiber 210 may be disposed within housing tube 200 wherein optic fiber distal end 211 may be adjacent to housing tube distal end 201. Illustratively, optic fiber 210 may be disposed within housing tube 200 wherein a portion of optic fiber 210 may be adjacent to a portion of first housing tube portion 220. In one or more embodiments, a portion of optic fiber 210 may be fixed to an inner portion of housing tube 200, e.g., by an adhesive or any suitable fixation means.

Illustratively, a cable 710 may be disposed within housing tube 200. In one or more embodiments, cable 710 may comprise a cable distal end 711 and a cable proximal end 712. Illustratively, cable 710 may be disposed within housing tube 200 wherein cable distal end 711 may be adjacent to housing tube distal end 201. In one or more embodiments, cable 710 may be disposed within housing tube 200 wherein a portion of cable 710 may be adjacent to a portion of first housing tube portion 220. Illustratively, a portion of cable 710 may be fixed to a portion of housing tube 200, e.g., by an adhesive or any suitable fixation means. For example, a portion of cable 710 may be fixed to housing tube 200 by a weld, a loop, a tie, etc.

Figure 8:
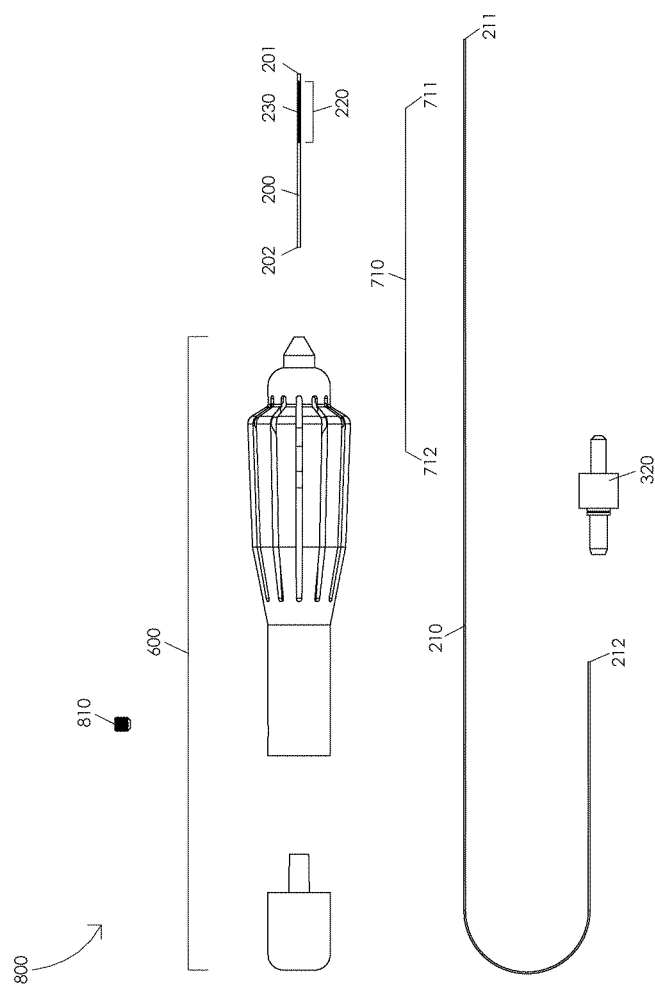
FIG. 8 is a schematic diagram illustrating an exploded view of a steerable laser probe assembly.

FIG. 8 is a schematic diagram illustrating an exploded view of a steerable laser probe assembly 800. In one or more embodiments, a steerable laser probe assembly 800 may comprise a handle 600, a housing tube 200 having a housing tube distal end 201 and a housing tube proximal end 202, an optic fiber 210 having an optic fiber distal end 211 and an optic fiber proximal end 212, a cable 710 having a cable distal end 711 and a cable proximal end 712, a fixation mechanism 810, and a light source interface 320. Illustratively, light source interface 320 may be configured to interface with optic fiber 210, e.g., at optic fiber proximal end 212. In one or more embodiments, light source interface 320 may comprise a standard light source connecter, e.g., an SMA connector.

Illustratively, a portion of housing tube 200 may be fixed to a portion of handle 600, e.g., housing tube proximal end 202 may be fixed to handle distal end 601. In one or more embodiments, a portion of housing tube 200 may be fixed to a portion of handle 600, e.g., by an adhesive or any suitable fixation means. Illustratively, a portion of housing tube 200 may be disposed within housing tube housing 650, e.g., housing tube proximal end 202 may be disposed within housing tube housing 650. In one or more embodiments, a portion of housing tube 200 may be fixed within housing tube housing 650, e.g., by an adhesive or any suitable fixation means. For example, housing tube 200 may be fixed within housing tube housing 650 by a press fit, a weld, a setscrew, etc.

Illustratively, optic fiber 210 may be disposed within inner bore 640, housing tube housing 650, and housing tube 200. In one or more embodiments, optic fiber 210 may be disposed within housing tube 200 wherein optic fiber distal end 211 may be adjacent to housing tube distal end 201. Illustratively, optic fiber 210 may be disposed within housing tube 200 wherein a portion of optic fiber 210 may be adjacent to a portion of first housing tube portion 220. In one or more embodiments, a portion of optic fiber 210 may be fixed to a portion of housing tube 200, e.g., by an adhesive or any suitable fixation means. Illustratively, cable 710 may be disposed within cable housing 645, inner bore 640, housing tube housing 650, and housing tube 200. In one or more embodiments, cable 710 may be disposed within housing tube 200 wherein cable distal end 711 may be adjacent to housing tube distal end 201. Illustratively, cable 710 may be disposed within housing tube 200 wherein a portion of cable 710 may be adjacent to a portion of first housing tube portion 220. In one or more embodiments, a portion of cable 710 may be fixed to a portion of housing tube 200, e.g., by an adhesive or any suitable fixation means. For example, a portion of cable 710 may be fixed to housing tube 200 by a weld, a loop, a tie, etc. Illustratively, a portion of cable 710 may be fixed within cable housing 645, e.g., by an adhesive or any suitable fixation means. In one or more embodiments, fixation mechanism 810 may be configured to fix a portion of cable 710 within cable housing 645, e.g., fixation mechanism 810 may be disposed within fixation mechanism housing 615 and cable housing 645. Illustratively, fixation mechanism 810 may be configured to fix a portion of cable 710 within cable housing 645, e.g., by a press fit or any suitable fixation means. In one or more embodiments, fixation mechanism 810 may comprise a set screw, e.g., configured to fix a portion of cable within cable housing 645.

Illustratively, a compression of actuation structure 120 may be configured to extend actuation structure distal end 121 relative to actuation structure proximal end 122. In one or more embodiments, an extension of actuation structure distal end 121 relative to actuation structure proximal end 122 may be configured to extend handle distal end 601 relative to handle proximal end 602. Illustratively, an extension of handle distal end 601 relative to handle proximal end 602 may be configured to extend housing tube 200 relative to handle proximal end 602. In one or more embodiments, an extension of housing tube 200 relative to handle proximal end 602 may be configured to extend housing tube 200 relative to cable 710. Illustratively, a portion of cable 710, e.g., a portion of cable 710 fixed to housing tube 200, may be configured to resist an extension of housing tube 200 relative to cable 710. In one or more embodiments, an extension of housing tube 200 relative to cable 710 may be configured to compress a portion of housing tube 200, e.g., a portion of cable 710 fixed to a portion of housing tube 200 may be configured compress a portion of housing tube 200. Illustratively, a compression of a portion of housing tube 200, e.g., first housing tube portion 220, may be configured to cause housing tube 200 to gradually curve. In one or more embodiments, a gradual curving of housing tube 200 may be configured to gradually curve optic fiber 210. Illustratively, a compression of actuation structure 120 may be configured to gradually curve housing tube 200. In one or more embodiments, a compression of actuation structure 120 may be configured to gradually curve optic fiber 210.

Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract handle distal end 601 relative to handle proximal end 602. Illustratively, a retraction of handle distal end 601 relative to handle proximal end 602 may be configured to retract housing tube 200 relative to handle proximal end 602. In one or more embodiments, a retraction of housing tube 200 relative to handle proximal end 602 may be configured to retract housing tube 200 relative to cable 710. Illustratively, a portion of cable 710, e.g., a portion of cable 710 fixed to housing tube 200, may be configured to facilitate a retraction of housing tube 200 relative to cable 710. In one or more embodiments, a retraction of housing tube 200 relative to cable 710 may be configured to decompress a portion of housing tube 200, e.g., a portion of cable 710 fixed to a portion of housing tube 200 may be configured decompress a portion of housing tube 200. Illustratively, a decompression of a portion of housing tube 200, e.g., first housing tube portion 220, may be configured to cause housing tube 200 to gradually straighten. In one or more embodiments, a gradual straightening of housing tube 200 may be configured to gradually straighten optic fiber 210. Illustratively, a decompression of actuation structure 120 may be configured to gradually straighten housing tube 200. In one or more embodiments, a decompression of actuation structure 120 may be configured to gradually straighten optic fiber 210.

Figure 9A:
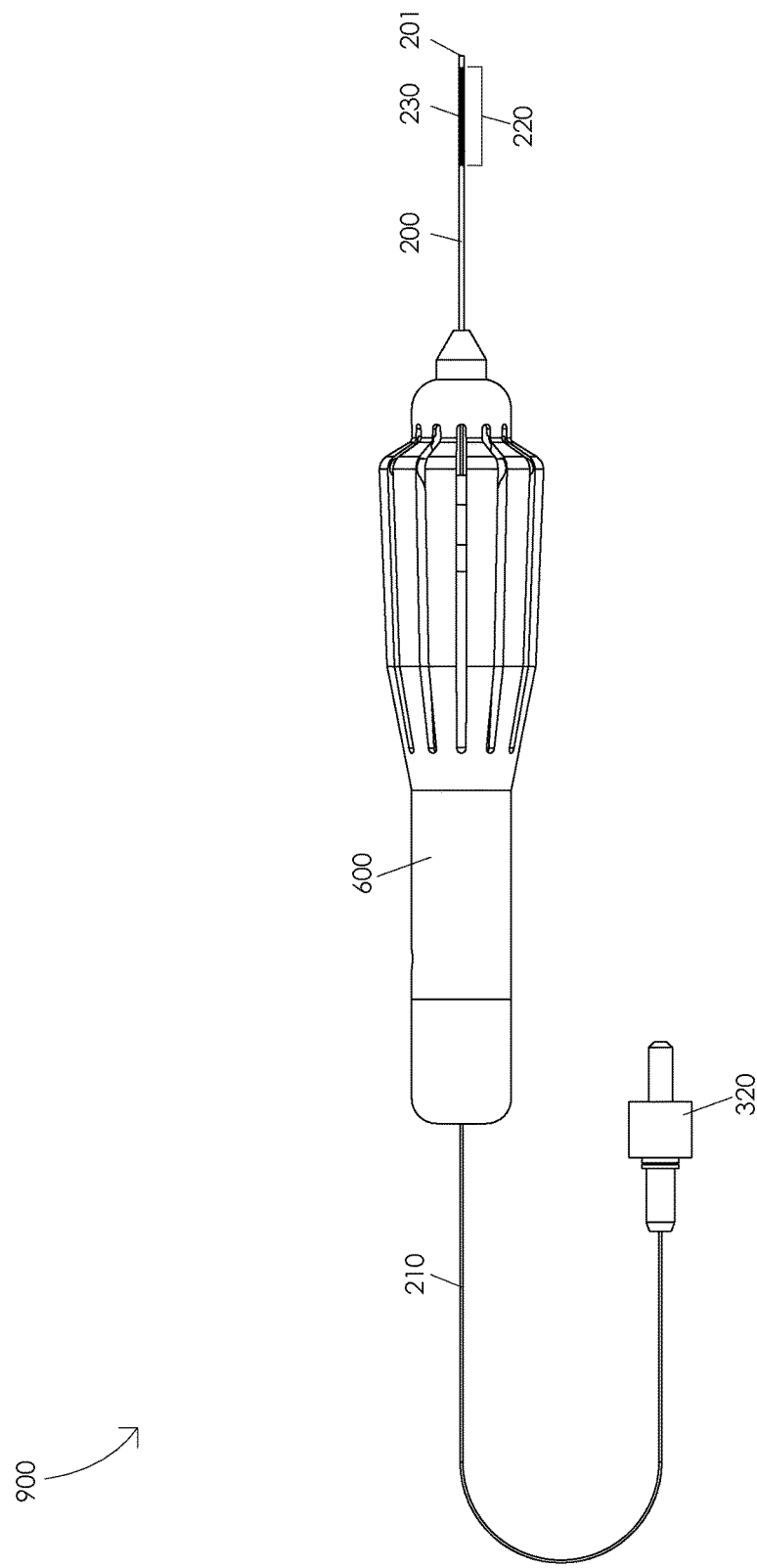
FIGS. 9A, 9B, 9C, 9D, and 9E are schematic diagrams illustrating a gradual curving of an optic fiber.

FIGS. 9A, 9B, 9C, 9D, and 9E are schematic diagrams illustrating a gradual curving of an optic fiber 210. FIG. 9A illustrates a straight optic fiber 900. In one or more embodiments, optic fiber 210 may comprise a straight optic fiber 900, e.g., when actuation structure 120 is fully decompressed. Illustratively, optic fiber 210 may comprise a straight optic fiber 900, e.g., when housing tube 200 is fully retracted relative to cable 710. For example, optic fiber 210 may comprise a straight optic fiber 900, e.g., when first housing tube portion 220 is fully decompressed. Illustratively, a line tangent to optic fiber distal end 211 may be parallel to a line tangent to housing tube proximal end 202, e.g., when optic fiber 210 comprises a straight optic fiber 900.

Figure 9B:
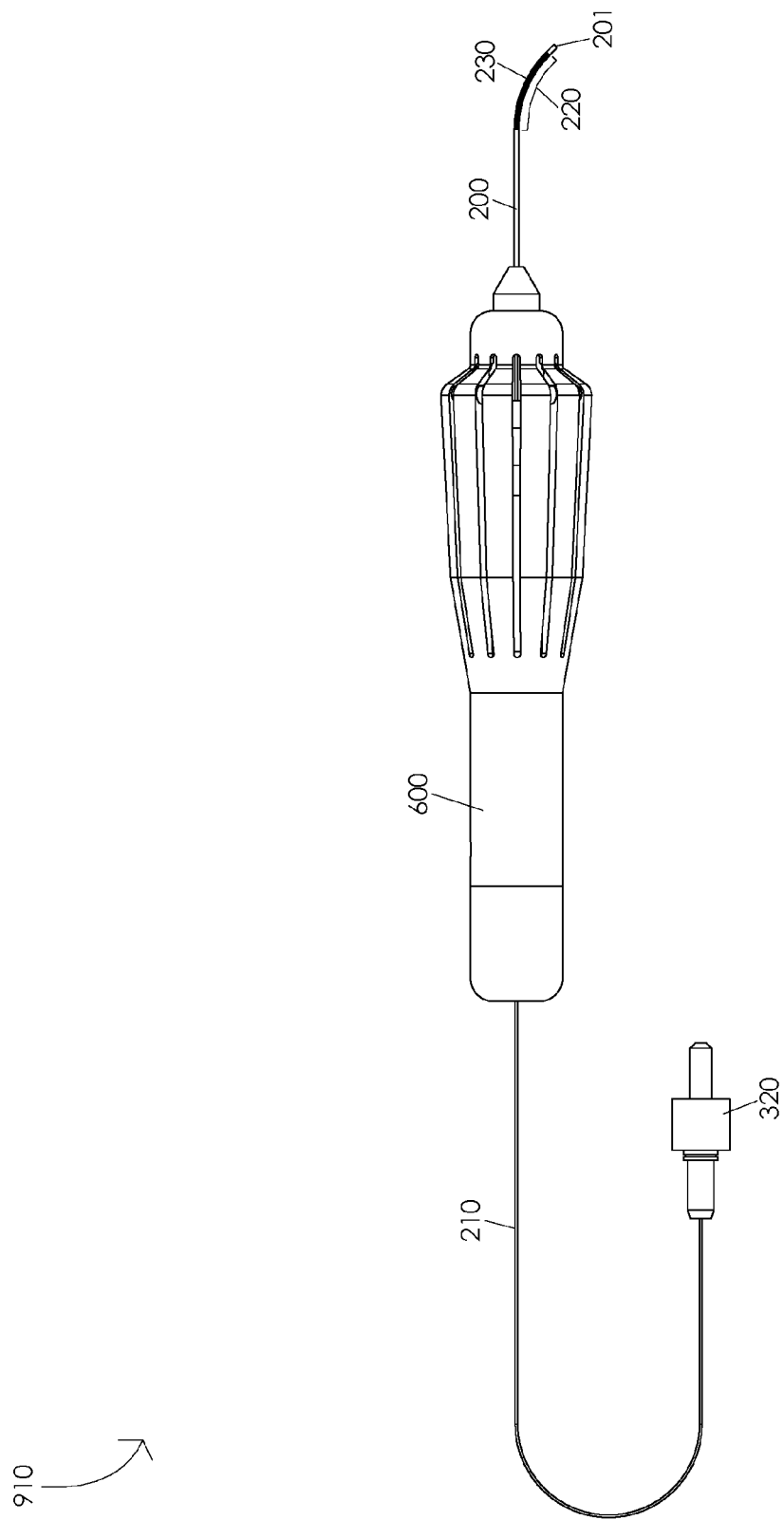

FIG. 9B illustrates an optic fiber in a first curved position 910. In one or more embodiments, a compression of actuation structure 120 may be configured to gradually curve optic fiber 210 from a straight optic fiber 900 to an optic fiber in a first curved position 910. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to cable 710. Illustratively, an extension of housing tube 200 relative to cable 710 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from a straight optic fiber 900 to an optic fiber in a first curved position 910. In one or more embodiments, a line tangent to optic fiber distal end 211 may intersect a line tangent to housing tube proximal end 202 at a first angle, e.g., when optic fiber 210 comprises an optic fiber in a first curved position 910. In one or more embodiments, the first angle may comprise any angle greater than zero degrees. For example, the first angle may comprise a 45 degree angle.

Figure 9C:
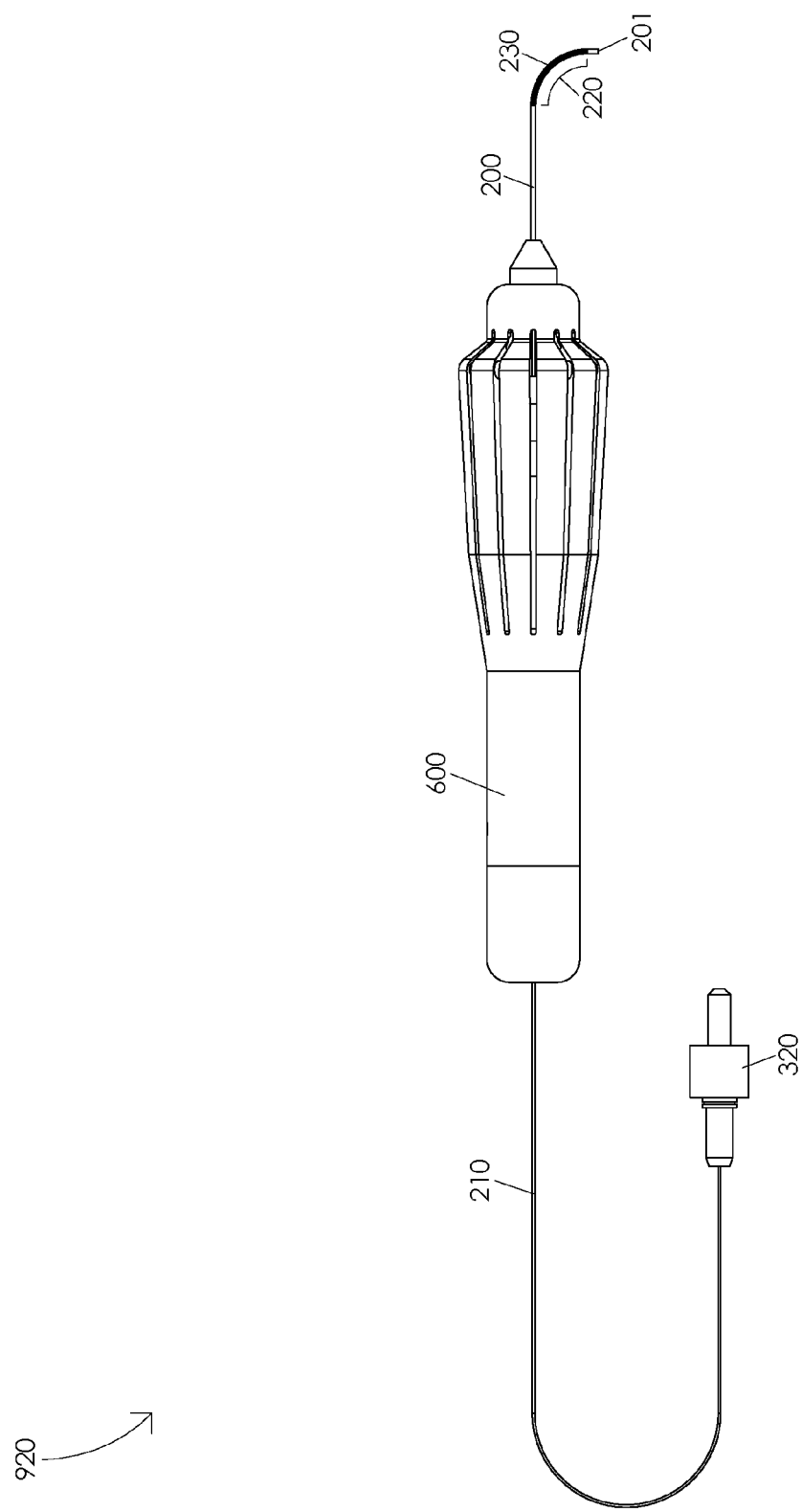

FIG. 9C illustrates an optic fiber in a second curved position 920. In one or more embodiments, a compression of actuation structure 120 may be configured to gradually curve optic fiber 210 from an optic fiber in a first curved position 910 to an optic fiber in a second curved position 920. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to cable 710. Illustratively, an extension of housing tube 200 relative to cable 710 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from an optic fiber in a first curved position 910 to an optic fiber in a second curved position 920. In one or more embodiments, a line tangent to optic fiber distal end 211 may intersect a line tangent to housing tube proximal end 202 at a second angle, e.g., when optic fiber 210 comprises an optic fiber in a second curved position 920. In one or more embodiments, the second angle may comprise any angle greater than the first angle. For example, the second angle may comprise a 90 degree angle.

Figure 9D:
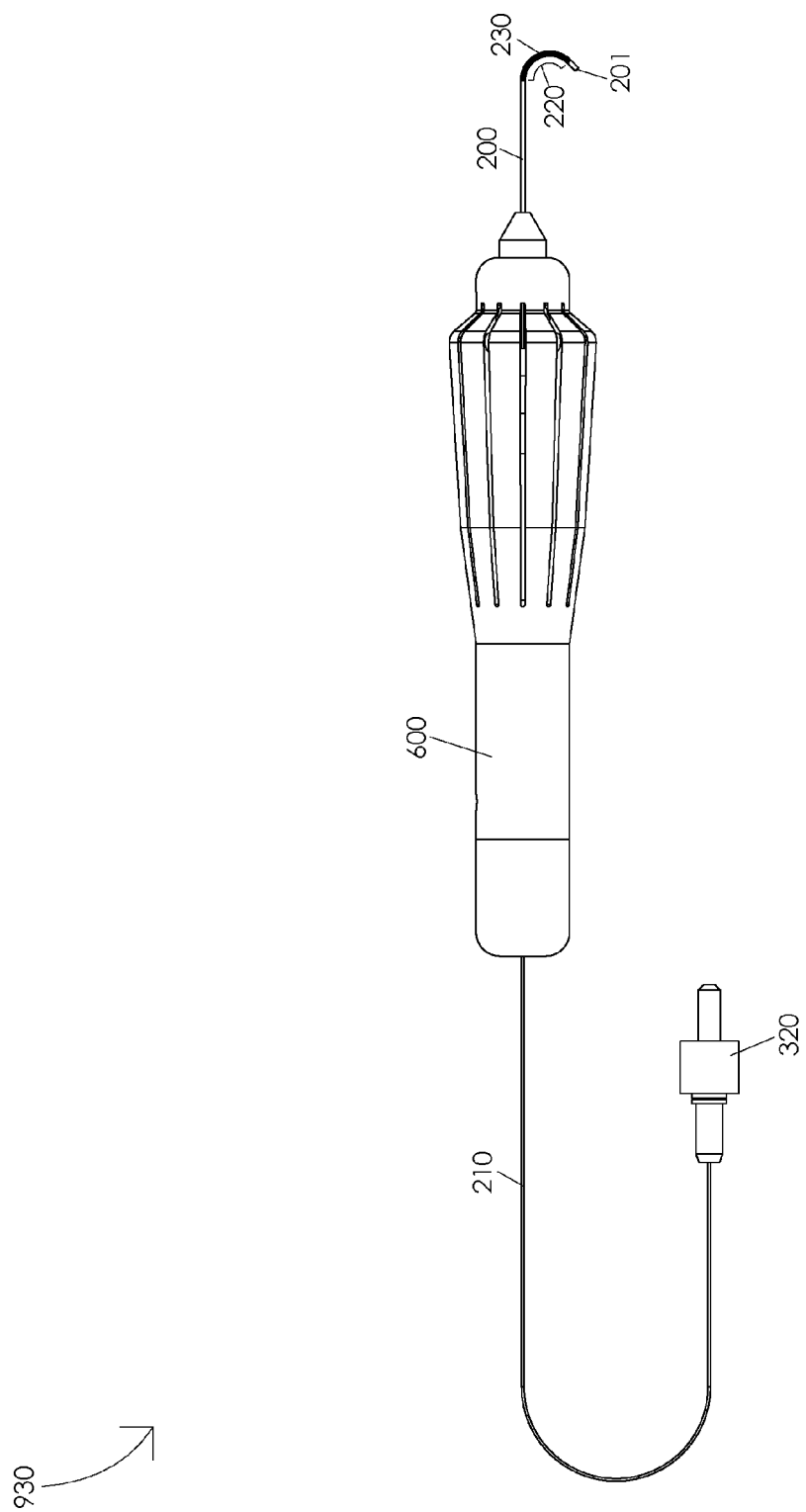

FIG. 9D illustrates an optic fiber in a third curved position 930. In one or more embodiments, a compression of actuation structure 120 may be configured to gradually curve optic fiber 210 from an optic fiber in a second curved position 920 to an optic fiber in a third curved position 930. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to cable 710. Illustratively, an extension of housing tube 200 relative to cable 710 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from an optic fiber in a second curved position 920 to an optic fiber in a third curved position 930. In one or more embodiments, a line tangent to optic fiber distal end 211 may intersect a line tangent to housing tube proximal end 202 at a third angle, e.g., when optic fiber 210 comprises an optic fiber in a third curved position 930. In one or more embodiments, the third angle may comprise any angle greater than the second angle. For example, the third angle may comprise a 135 degree angle.

Figure 9E:
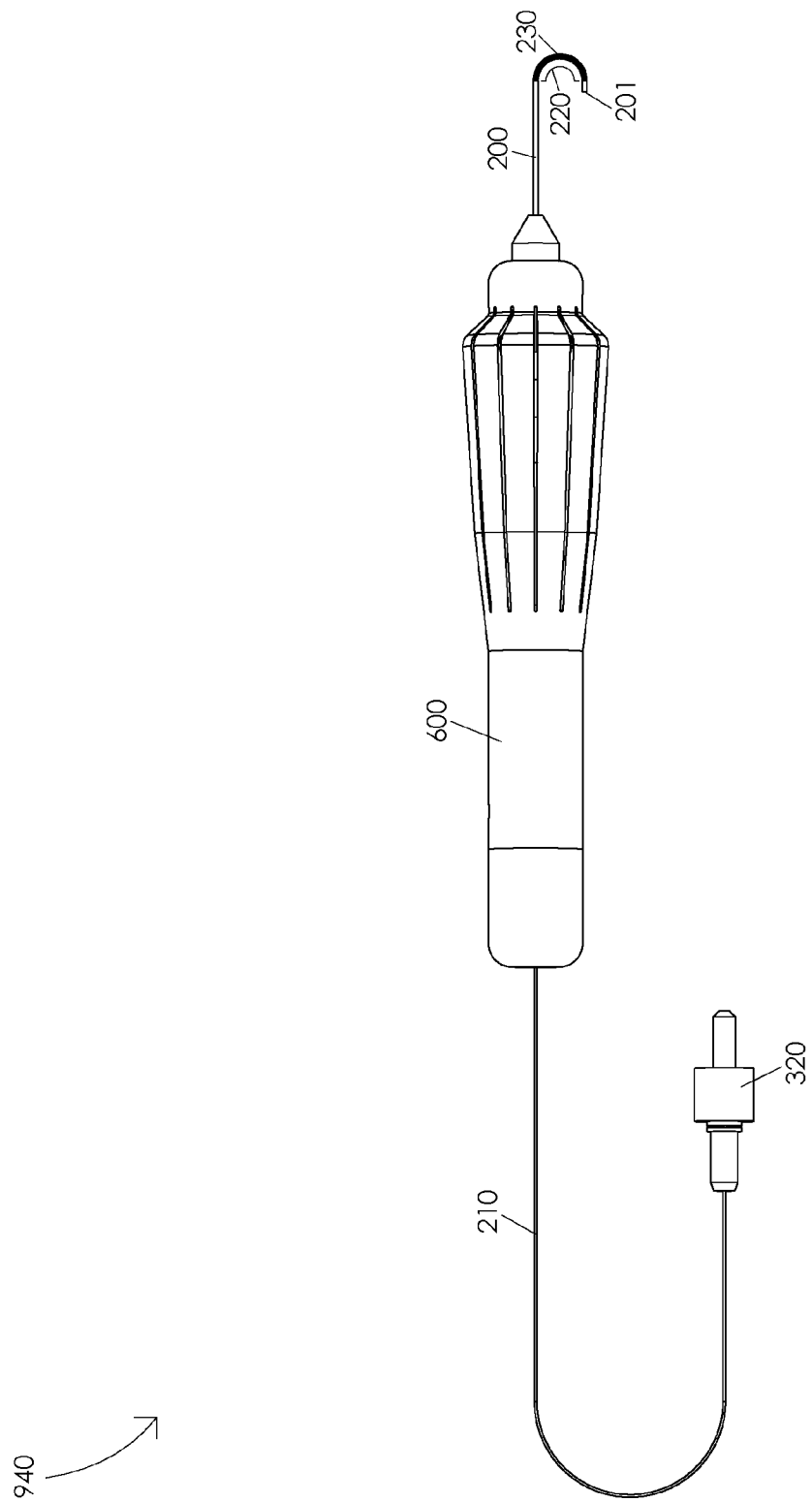

FIG. 9E illustrates an optic fiber in a fourth curved position 940. In one or more embodiments, a compression of actuation structure 120 may be configured to gradually curve optic fiber 210 from an optic fiber in a third curved position 930 to an optic fiber in a fourth curved position 940. Illustratively, a compression of actuation structure 120 may be configured to extend actuation structure distal end 121 relative to actuation structure proximal end 122. In one or more embodiments, an extension of actuation structure distal 121 end relative to actuation structure proximal end 122 may be configured to extend housing tube 200 relative to cable 710. Illustratively, an extension of housing tube 200 relative to cable 710 may be configured to compress a portion of housing tube 200, e.g., first housing tube portion 220. In one or more embodiments, a compression of a portion of housing tube 200 may be configured to gradually curve housing tube 200. Illustratively, a gradual curving of housing tube 200 may be configured to gradually curve optic fiber 210, e.g., from an optic fiber in a third curved position 930 to an optic fiber in a fourth curved position 940. In one or more embodiments, a line tangent to optic fiber distal end 211 may be parallel to a line tangent to housing tube proximal end 202, e.g., when optic fiber 210 comprises an optic fiber in a fourth curved position 940.

In one or more embodiments, one or more properties of a steerable laser probe may be adjusted to attain one or more desired steerable laser probe features. Illustratively, a length that housing tube distal end 201 extends from handle distal end 601 may be adjusted to vary an amount of compression of actuation structure 120 configured to curve housing tube 200 to a particular curved position. In one or more embodiments, a stiffness of first housing tube portion 220 or a stiffness of second housing tube portion 230 may be adjusted to vary an amount of compression of actuation structure 120 configured to curve housing tube 200 to a particular curved position. Illustratively, a material comprising first housing tube portion 220 or a material comprising second housing tube portion 230 may be adjusted to vary an amount of compression of actuation structure 120 configured to curve housing tube 200 to a particular curved position.

In one or more embodiments, a number of apertures in housing tube 200 may be adjusted to vary an amount of compression of actuation structure 120 configured to curve housing tube 200 to a particular curved position. Illustratively, a location of one or more apertures in housing tube 200 may be adjusted to vary an amount of compression of actuation structure 120 configured to curve housing tube 200 to a particular curved position. In one or more embodiments, a geometry of one or more apertures in housing tube 200 may be adjusted to vary an amount of compression of actuation structure 120 configured to curve housing tube 200 to a particular curved position. Illustratively, a geometry of one or more apertures in housing tube 200 may be uniform, e.g., each aperture of the one or more apertures may have a same geometry. In one or more embodiments, a geometry of one or more apertures in housing tube 200 may be nonuniform, e.g., a first aperture in housing tube 200 may have a first geometry and a second aperture in housing tube 200 may have a second geometry. Illustratively, a geometry or location of one or more apertures in housing tube 200 may be optimized to evenly distribute an applied force. For example, a geometry or location of one or more apertures in housing tube 200 may be optimized to evenly distribute a compressive force applied to first housing tube portion 220.

Illustratively, a stiffness of first housing tube portion 220 or a stiffness of second housing tube portion 230 may be adjusted to vary a bend radius of housing tube 200. In one or more embodiments, a stiffness of first housing tube portion 220 or a stiffness of second housing tube portion 230 may be adjusted to vary a radius of curvature of housing tube 200, e.g., when housing tube 200 is in a particular curved position. Illustratively, a number of apertures in housing tube 200 may be adjusted to vary a bend radius of housing tube 200. In one or more embodiments, a number of apertures in housing tube 200 may be adjusted to vary a radius of curvature of housing tube 200, e.g., when housing tube 200 is in a particular curved position. Illustratively, a location or a geometry of one or more apertures in housing tube 200 may be adjusted to vary a bend radius of housing tube 200. In one or more embodiments, a location or a geometry of one or more apertures in housing tube 200 may be adjusted to vary a radius of curvature of housing tube 200, e.g., when housing tube 200 is in a particular curved position. Illustratively, a geometry of actuation structure 120 may be adjusted to vary an amount of compression of actuation structure 120 configured to curve housing tube 200 to a particular curved position. In one or more embodiments, one or more locations within housing tube 200 wherein optic fiber 210 may be fixed to a portion of housing tube 200 may be adjusted to vary an amount of compression of actuation structure 120 configured to curve housing tube 200 to a particular curved position.

In one or more embodiments, at least a portion of optic fiber 210 may be enclosed in an optic fiber sleeve configured to, e.g., protect optic fiber 210, vary a stiffness of optic fiber 210, vary an optical property of optic fiber 210, etc. Illustratively, optic fiber 210 may comprise a buffer, a cladding disposed in the buffer, and a core disposed in the cladding. In one or more embodiments, at least a portion of optic fiber 210 may comprise a buffer configured to protect an optical property of optic fiber 210. Illustratively, at least a portion of optic fiber 210 may comprise a buffer configured to protect an optical layer of optic fiber 210, e.g., the buffer may protect an optical layer of a curved portion of optic fiber 210. In one or more embodiments, at least a portion of optic fiber 210 may comprise a polyimide buffer configured to protect an optical property of optic fiber 210. For example, at least a portion of optic fiber 210 may comprise a Kapton buffer configured to protect an optical property of optic fiber 210.

Illustratively, a steerable laser probe may be configured to indicate, e.g., to a surgeon, a direction that optic fiber 210 may curve, e.g., due to a compression of actuation structure 120. In one or more embodiments, a portion of a steerable laser probe, e.g., handle 600, may be marked in a manner configured to indicate a direction that optic fiber 210 may curve. For example, a portion of handle 600 may comprise an arrow marking configured to indicate a direction that optic fiber 210 may curve. Illustratively, a portion of housing tube 200 may comprise a mark configured to indicate a direction that optic fiber 210 may curve. In one or more embodiments, housing tube 200 may comprise a slight curve, e.g., a curve less than 7.5 degrees, when actuation structure 120 is fully decompressed. Illustratively, housing tube 200 may comprise a slight curve, e.g., a curve equal to or greater than 7.5 degrees, when actuation structure 120 is fully decompressed. In one or more embodiments, housing tube 200 may comprise a slight curve configured to indicate a direction that optic fiber 210 may curve, e.g., due to a compression of actuation structure 120.

In one or more embodiments, a location wherein cable 710 may be fixed to housing tube 200 may be adjusted to vary an amount of compression of actuation structure 120 configured to curve housing tube 200 to a particular curved position. For example, a portion of cable 710 may be fixed to an outer portion of housing tube 200. Illustratively, cable 710 may be fixed to housing tube 200 at a plurality of fixation points, e.g., to vary one or more properties of a steerable laser probe. In one or more embodiments, a length of cable 710 may be adjusted to vary an amount of compression of actuation structure 120 configured to curve housing tube 200 to a particular curved position. Illustratively, a steerable laser probe may comprise one or more redundant cables 710. In one or more embodiments, one or more redundant cables 710 may be configured to maintain a particular curved position of housing tube 200, e.g., in the event that cable 710 breaks or fails. Illustratively, one or more redundant cables 710 may be configured to maintain a particular curved position of housing tube 200, e.g., in the event that a cable 710 fixation means fails. In one or more embodiments, one or more redundant cables 710 may be configured to maintain a particular curved position of housing tube 200, e.g., in the event that cable 710 is no longer configured to maintain the particular curved position of housing tube 200. Illustratively, one or more redundant cables 710 may be configured to maintain a particular curved position of housing tube 200 wherein cable 710 is also configured to maintain the particular curved position of housing tube 200.

In one or more embodiments, housing tube 200 may comprise an access window configured to allow access to a portion cable 710. Illustratively, cable 710 may be fixed to a portion of housing tube 200, e.g., by looping a portion of cable 710 through an aperture in housing tube 200. In one or more embodiments, cable 710 may be fixed to a portion of housing tube 200, e.g., by a purely mechanical means. For example, cable 710 may be fixed to a portion of housing tube 200 in a manner other than by an adhesive, a weld, etc. Illustratively, cable 710 may be fixed to a portion of housing tube 200 wherein a portion of cable 710 is configured to fail at a first applied failure force and a fixation means that fixes a portion of cable 710 to a portion of housing tube 200 is configured to fail at a second applied failure force. In one or more embodiments, the second applied failure force may be greater than the first applied failure force.

Figure 10A:
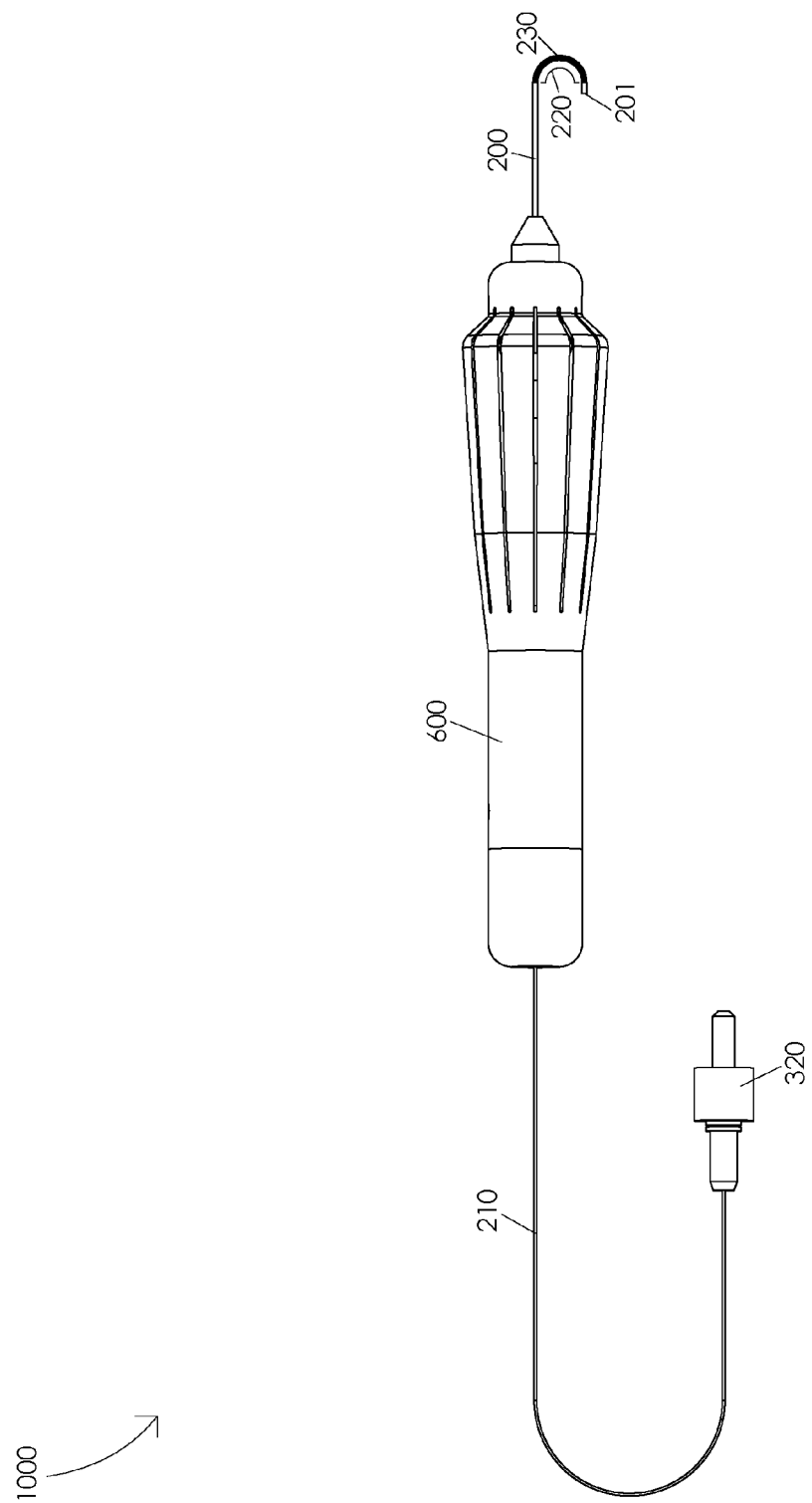
FIGS. 10A, 10B, 10C, 10D, and 10E are schematic diagrams illustrating a gradual straightening of an optic fiber.

FIGS. 10A, 10B, 10C, 10D, and 10E are schematic diagrams illustrating a gradual straightening of an optic fiber 210. FIG. 10A illustrates a fully curved optic fiber 1000. In one or more embodiments, optic fiber 210 may comprise a fully curved optic fiber 1000, e.g., when actuation structure 120 is fully compressed. Illustratively, optic fiber 210 may comprise a fully curved optic fiber 1000, e.g., when housing tube 200 is fully extended relative to wire 710. For example, optic fiber 210 may comprise a fully curved optic fiber 1000, e.g., when first housing tube portion 220 is fully compressed. In one or more embodiments, a line tangent to optic fiber distal end 211 may be parallel to a line tangent to housing tube proximal end 202, e.g., when optic fiber 210 comprises a fully curved optic fiber 1000.

Figure 10B:
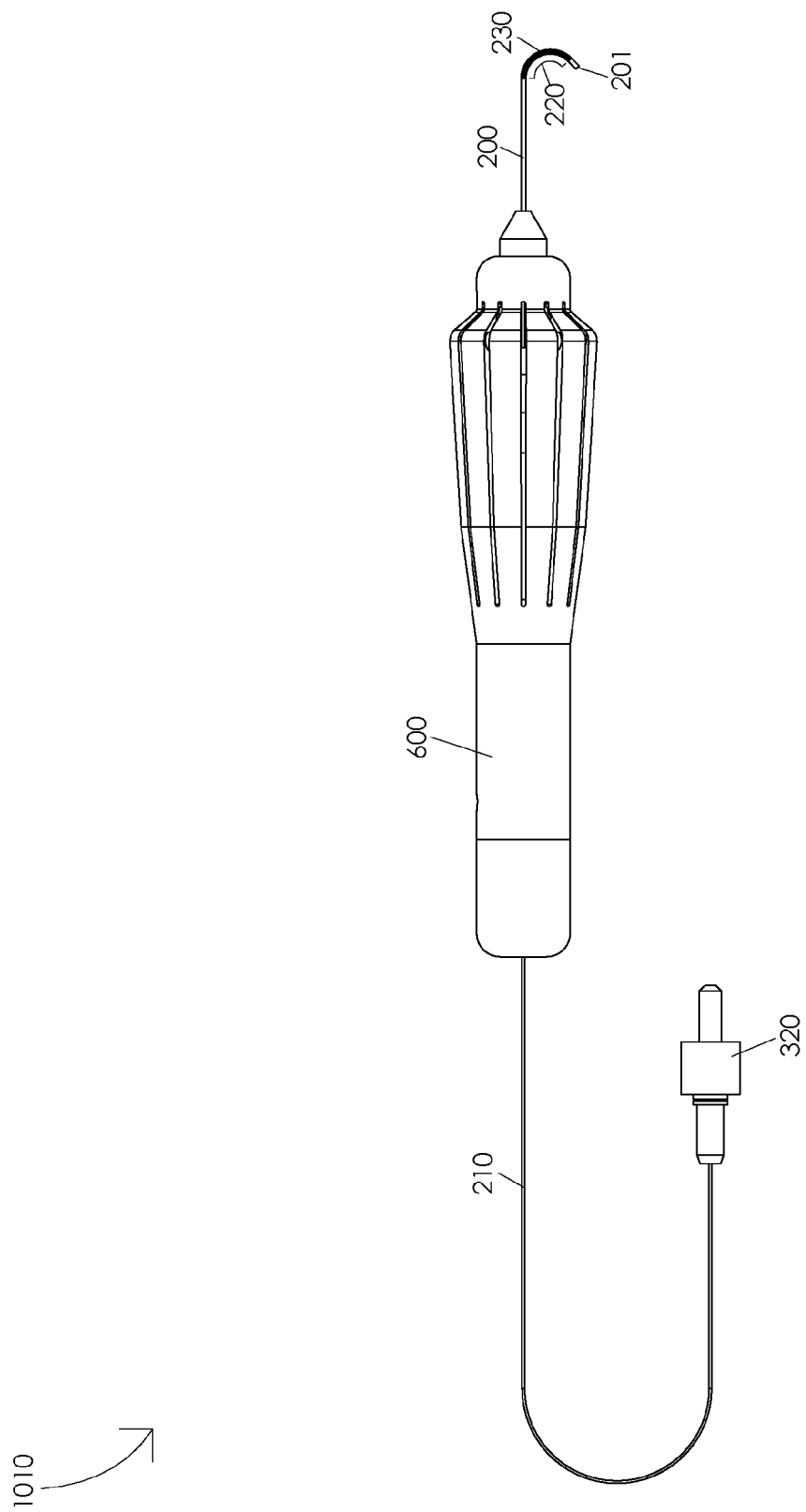

FIG. 10B illustrates an optic fiber in a first partially straightened position 1010. In one or more embodiments, a decompression of actuation structure 120 may be configured to gradually straighten optic fiber 210 from a fully curved optic fiber 1000 to an optic fiber in a first partially straightened position 1010. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract housing tube 200 relative to cable 710. Illustratively, a portion of cable 710, e.g., a portion of cable 710 fixed to a portion of housing tube 200, may be configured to facilitate a retraction of housing tube 200 relative to cable 710. In one or more embodiments, a retraction of housing tube 200 relative to cable 710 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from a fully curved optic fiber 1000 to an optic fiber in a first partially straightened position 1010. Illustratively, a line tangent to optic fiber distal end 211 may intersect a line tangent to housing tube proximal end 202 at a first partially straightened angle, e.g., when optic fiber 210 comprises an optic fiber in a first partially straightened position 1010. In one or more embodiments, the first partially straightened angle may comprise any angle less than 180 degrees. For example, the first partially straightened angle may comprise a 135 degree angle.

Figure 10C:
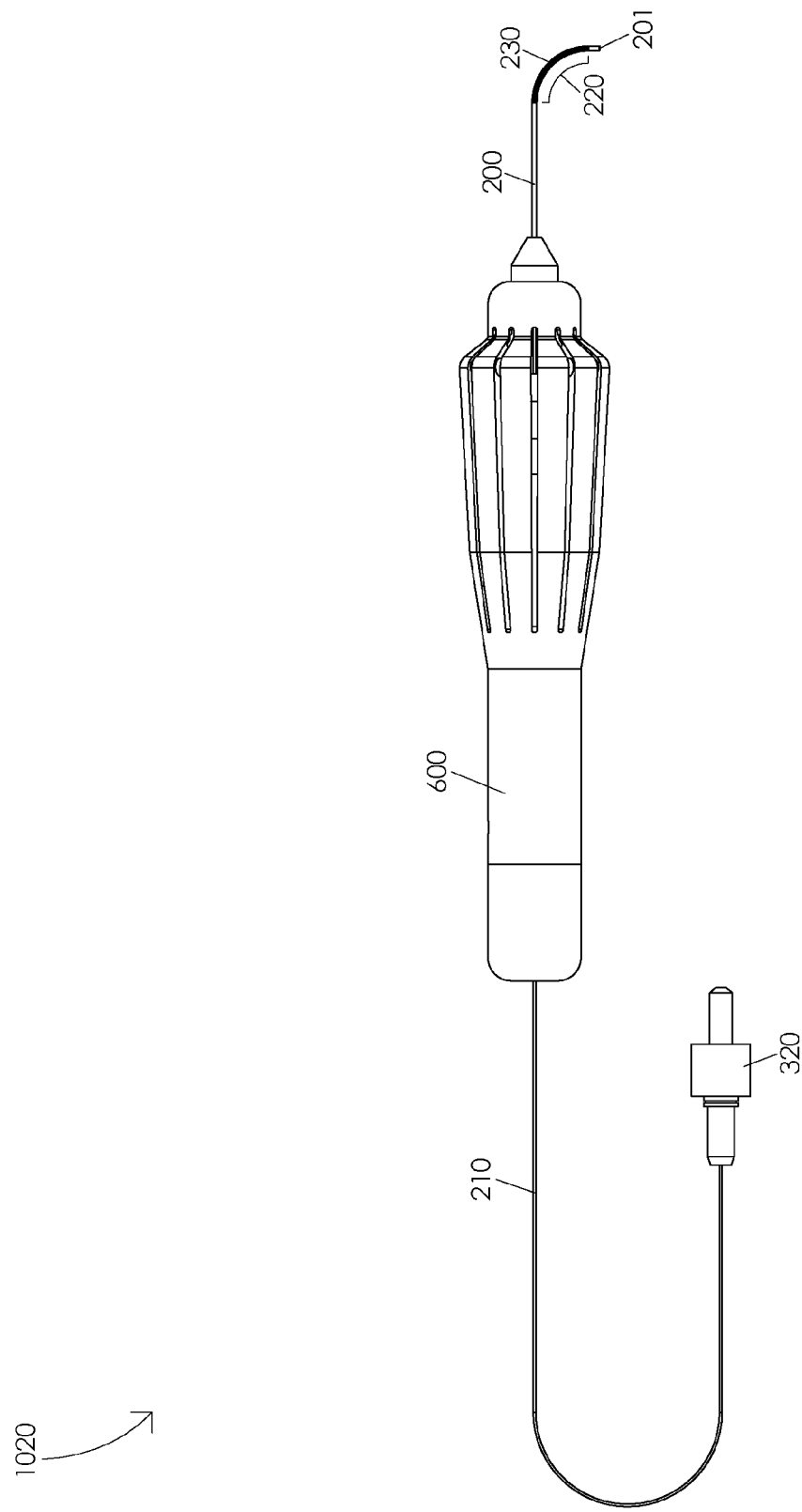

FIG. 10C illustrates an optic fiber in a second partially straightened position 1020. In one or more embodiments, a decompression of actuation structure 120 may be configured to gradually straighten optic fiber 210 from an optic fiber in a first partially straightened position 1010 to an optic fiber in a second partially straightened position 1020. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract housing tube 200 relative to cable 710. Illustratively, a portion of cable 710, e.g., a portion of cable 710 fixed to a portion of housing tube 200, may be configured to facilitate a retraction of housing tube 200 relative to cable 710. In one or more embodiments, a retraction of housing tube 200 relative to cable 710 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from an optic fiber in a first partially straightened position 1010 to an optic fiber in a second partially straightened position 1020. Illustratively, a line tangent to optic fiber distal end 211 may intersect a line tangent to housing tube proximal end 202 at a second partially straightened angle, e.g., when optic fiber 210 comprises an optic fiber in a second partially straightened position 1020. In one or more embodiments, the second partially straightened angle may comprise any angle less than the first partially straightened angle. For example, the second partially straightened angle may comprise a 90 degree angle.

Figure 10D:
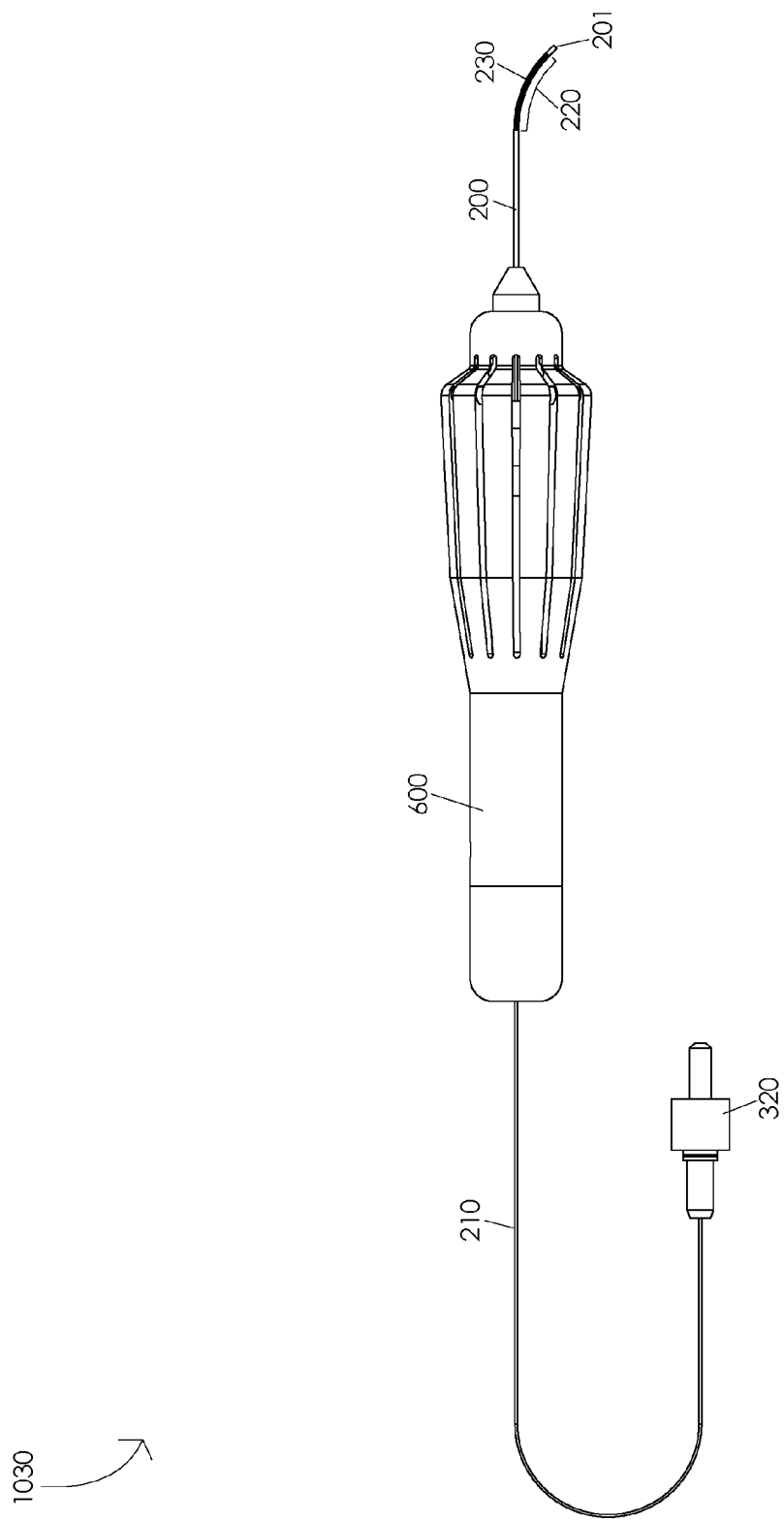

FIG. 10D illustrates an optic fiber in a third partially straightened position 1030. In one or more embodiments, a decompression of actuation structure 120 may be configured to gradually straighten optic fiber 210 from an optic fiber in a second partially straightened position 1020 to an optic fiber in a third partially straightened position 1030. Illustratively, a decompression of actuation structure 120 may be configured to retract actuation structure distal end 121 relative to actuation structure proximal end 122. In one or more embodiments, a retraction of actuation structure distal end 121 relative to actuation structure proximal end 122 may be configured to retract housing tube 200 relative to cable 710. Illustratively, a portion of cable 710, e.g., a portion of cable 710 fixed to a portion of housing tube 200, may be configured to facilitate a retraction of housing tube 200 relative to cable 710. In one or more embodiments, a retraction of housing tube 200 relative to cable 710 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from an optic fiber in a second partially straightened position 1020 to an optic fiber in a third partially straightened position 1030. Illustratively, a line tangent to optic fiber distal end 211 may intersect a line tangent to housing tube proximal end 202 at a third partially straightened angle, e.g., when optic fiber 210 comprises an optic fiber in a third partially straightened position 1030. In one or more embodiments, the third partially straightened angle may comprise any angle less than the second partially straightened angle. For example, the third partially straightened angle may comprise a 45 degree angle.

Figure 10E:
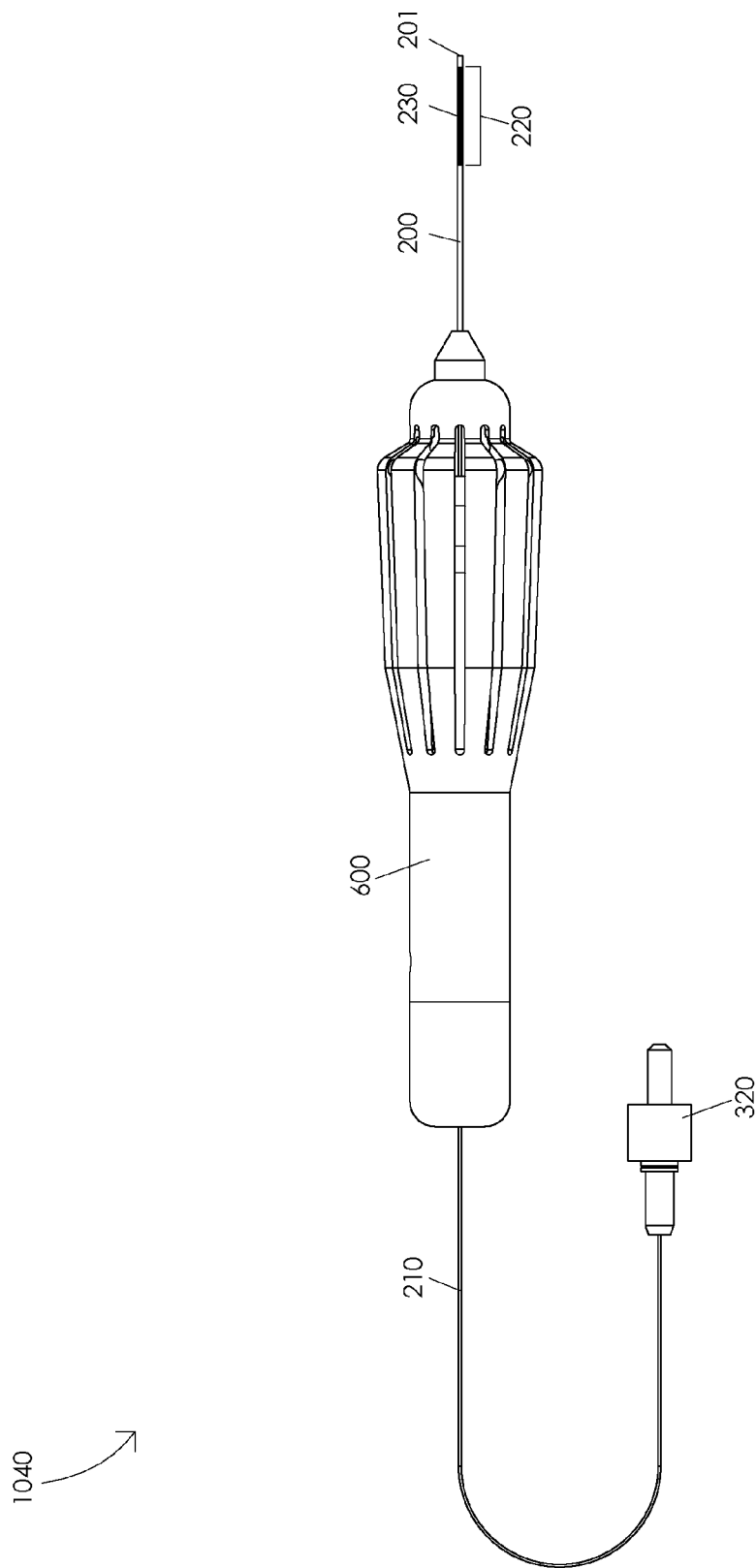

FIG. 10E illustrates an optic fiber in a fully straightened position 1040. In one or more embodiments, a decompression of actuation structure 120 may be configured to gradually straighten optic fiber 210 from an optic fiber in a third partially straightened position 1030 to an optic fiber in a fully straightened position 1040. Illustratively, a decompression of actuation structure 120 may be configured to retract actuation structure distal end 121 relative to actuation structure proximal end 122. In one or more embodiments, a refraction of actuation structure distal end 121 relative to actuation structure proximal end 122 may be configured to retract housing tube 200 relative to cable 710. Illustratively, a portion of cable 710, e.g., a portion of cable 710 fixed to a portion of housing tube 200, may be configured to facilitate a retraction of housing tube 200 relative to cable 710. In one or more embodiments, a retraction of housing tube 200 relative to cable 710 may be configured to decompress a portion of housing tube 200, e.g., first housing tube portion 220. Illustratively, a decompression of a portion of housing tube 200 may be configured to gradually straighten housing tube 200. In one or more embodiments, a gradual straightening of housing tube 200 may be configured to gradually straighten optic fiber 210, e.g., from an optic fiber in a third partially straightened position 1030 to an optic fiber in a fully straightened position 1040. Illustratively, a line tangent to optic fiber distal end 211 may be parallel to a line tangent to housing tube proximal end 202, e.g., when optic fiber 210 comprises an optic fiber in a fully straightened position 1040.

Illustratively, a surgeon may aim optic fiber distal end 211 at any of a plurality of targets within an eye, e.g., to perform a photocoagulation procedure, to illuminate a surgical target site, etc. In one or more embodiments, a surgeon may aim optic fiber distal end 211 at any target within a particular transverse plane of the inner eye by, e.g., rotating handle 600 to orient housing tube 200 in an orientation configured to cause a curvature of housing tube 200 within the particular transverse plane of the inner eye and varying an amount of compression of actuation structure 120. Illustratively, a surgeon may aim optic fiber distal end 211 at any target within a particular sagittal plane of the inner eye by, e.g., rotating handle 600 to orient housing tube 200 in an orientation configured to cause a curvature of housing tube 200 within the particular sagittal plane of the inner eye and varying an amount of compression of actuation structure 120. In one or more embodiments, a surgeon may aim optic fiber distal end 211 at any target within a particular frontal plane of the inner eye by, e.g., varying an amount of compression of actuation structure 120 to orient a line tangent to optic fiber distal end 211 wherein the line tangent to optic fiber distal end 211 is within the particular frontal plane of the inner eye and rotating handle 600. Illustratively, a surgeon may aim optic fiber distal end 211 at any target located outside of the particular transverse plane, the particular sagittal plane, and the particular frontal plane of the inner eye, e.g., by varying a rotational orientation of handle 600 and varying an amount of compression of actuation structure 120. In one or more embodiments, a surgeon may aim optic fiber distal end 211 at any target of a plurality of targets within an eye, e.g., without increasing a length of a portion of a steerable laser probe within the eye. Illustratively, a surgeon may aim optic fiber distal end 211 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a medical device, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   a handle having a handle distal end and a handle proximal end;
   an actuation structure of the handle having an actuation structure distal end and an actuation structure proximal end, the actuation structure having a density in a range of 0.02 to 0.06 pounds per cubic inch;
   a plurality of actuation arms of the actuation structure wherein each actuation arm of the plurality of actuation arms has at least one extension joint;
   a handle end plug of the handle, the handle end plug having a handle end plug distal end and a handle end plug proximal end wherein the handle end plug proximal end is the handle proximal end;
   a fixation mechanism housing of the handle;
   a single housing tube having a housing tube distal end and a housing tube proximal end, the housing tube having dimensions configured for performing ophthalmic surgical procedures wherein a portion of the housing tube is disposed in a housing tube housing of the handle;
   a first housing tube portion of the housing tube, the first housing tube portion having a first stiffness;
   a plurality of apertures of the first housing tube portion;
   a second housing tube portion of the housing tube, the second housing tube portion having a second stiffness;
   a cable housing of the handle end plug, the cable housing disposed between the actuation structure and the handle proximal end;
   a cable having a cable distal end and a cable proximal end, the cable disposed within an inner bore of the handle, the cable housing, and the housing tube wherein the cable distal end is adjacent to the housing tube distal end and wherein a first portion of the cable is adjacent to the plurality of apertures of the first housing tube portion and wherein the cable distal end is fixed to the housing tube by a weld and wherein a second portion of the cable is fixed in the cable housing by a fixation mechanism configured to fix the second portion of the cable in the cable housing by a press fit; and an optic fiber having an optic fiber distal end and an optic fiber proximal end, the optic fiber disposed within the inner bore of the handle within an inner bore of the handle and the housing tube wherein the optic fiber distal end is adjacent to the housing tube distal end, the optic fiber configured to transmit laser light and wherein a compression of the actuation structure is configured to extend the housing tube relative to the cable and wherein the cable is configured to resist an extension of the housing tube relative to the cable and wherein the cable is configured to compress the first housing tube portion.

2. The instrument of claim 1 wherein the density of the actuation structure is 0.041 pounds per cubic inch.

3. The instrument of claim 1 wherein the actuation structure has a mass in a range of 0.01 to 0.03 pounds.

4. The instrument of claim 3 wherein the mass of the actuation structure is 0.024 pounds.

5. The instrument of claim 1 wherein the actuation structure has a volume in a range of 0.3 to 0.7 cubic inches.

6. The instrument of claim 5 wherein the volume of the actuation structure is 0.577 cubic inches.

7. The instrument of claim 1 wherein the actuation structure has a surface area in a range of 10.0 to 20.0 square inches.

8. The instrument of claim 7 wherein the surface area of the actuation structure is 14.87 square inches.

9. The instrument of claim 1 wherein the actuation structure is manufactured from Nylon.

10. The instrument of claim 1 wherein the actuation structure is manufactured using selective laser sintering.

11. The instrument of claim 1 wherein the actuation structure is manufactured using 3D printing.

12. The instrument of claim 1 wherein the compression of the actuation structure is configured to gradually curve the optic fiber.

13. The instrument of claim 12 wherein the compression of the actuation structure is configured to extend the actuation structure distal end relative to the actuation structure proximal end in a range of 0.02 to 0.06 inches.

14. The instrument of claim 12 wherein the compression of the actuation structure is configured to increase a distance between the actuation structure distal end and the actuation structure proximal end in a range of 0.5 to 2.5 percent.

15. The instrument of claim 12 wherein the compression of the actuation structure is configured to gradually curve the optic fiber within an eye without increasing a length of the optic fiber within the eye.

16. The instrument of claim 1 wherein an application of a force having a magnitude in a range of 0.6 to 1.6 pounds to a portion of the actuation structure is configured to compress the actuation structure.

17. The instrument of claim 1 wherein a decompression of the actuation structure is configured to gradually straighten the optic fiber.

18. The instrument of claim 17 wherein the decompression of the actuation structure is configured to retract the actuation structure distal end relative to the actuation structure proximal end in a range of 0.02 to 0.06 inches.

19. The instrument of claim 17 wherein the decompression of the actuation structure is configured to decrease a distance between the actuation structure distal end and the actuation structure proximal end in a range of 0.5 to 2.5 percent.

20. The instrument of claim 1 further comprising:
a slight curve of the housing tube, the slight curve configured to indicate a direction that the optic fiber is configured to curve.

* * * * *